(12) United States Patent
Matuszewski et al.

(10) Patent No.: US 12,370,223 B2
(45) Date of Patent: *Jul. 29, 2025

(54) STERILE HUMAN PLACENTAL ALLOGRAFTS HAVING A PLURALITY OF SLITS, OPENINGS, AND/OR FENESTRATIONS FORMED THEREON

(71) Applicant: BioStem Technologies, Inc., Pompano Beach, FL (US)

(72) Inventors: Jason V. Matuszewski, Boca Raton, FL (US); Wendy W. Weston, Coral Springs, FL (US)

(73) Assignee: BioStem Technologies, Inc., Pompano Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/926,867

(22) Filed: Oct. 25, 2024

(65) Prior Publication Data

US 2025/0064862 A1   Feb. 27, 2025

Related U.S. Application Data

(63) Continuation of application No. 18/591,883, filed on Feb. 29, 2024, now Pat. No. 12,144,831, which is a (Continued)

(30) Foreign Application Priority Data

Oct. 14, 2022  (NL) ...................................... 2033318

(51) Int. Cl.
   *A61K 35/50*   (2015.01)
   *A61L 27/36*   (2006.01)
(52) U.S. Cl.
   CPC .......... *A61K 35/50* (2013.01); *A61L 27/3604* (2013.01)

(58) Field of Classification Search
   None
   See application file for complete search history.

(56) References Cited

U.S. PATENT DOCUMENTS

| 2,877,765 A | 3/1959 | Bunyan |
| 5,255,587 A | 10/1993 | Eichenberg et al. |

(Continued)

FOREIGN PATENT DOCUMENTS

| EP | 0399782 A2 | 4/1991 |
| WO | 9310722 A2 | 6/1993 |

(Continued)

OTHER PUBLICATIONS

International Preliminary Report on Patentability issued for PCT/US2023/026444; issued Dec. 18, 2024 (6 Pages).

(Continued)

*Primary Examiner* — Evelyn Y Pyla
(74) *Attorney, Agent, or Firm* — Shumaker, Loop & Kendrick, LLP

(57) ABSTRACT

A method of preparing sterile human placental allografts by providing a human placental tissue from a donor within 24 hours to 72 hours post-childbirth; removing any visible blood, blood clots, and/or blood components from the human placental tissue without scraping or scrubbing the human placental tissue to preserve structural integrity of the human placental tissue; washing the human placental tissue in an isotonic solution while maintaining the structural integrity of the human placental tissue; dehydrating the human placental tissue thereby forming the dehydrated human placental tissue; resizing the dehydrated human placental tissue into dehydrated human placental tissue portions having predetermined sizes; and sterilizing the dehydrated human placental tissue portions of step (e) thereby forming the sterile human placental allograft. Also (Continued)

disclosed is a sterile human placental allograft produced by the method.

14 Claims, 20 Drawing Sheets

Related U.S. Application Data continuation of application No. PCT/US2023/026444, filed on Jun. 28, 2023.

(60) Provisional application No. 63/356,628, filed on Jun. 29, 2022, provisional application No. 63/391,032, filed on Jul. 21, 2022, provisional application No. 63/395,426, filed on Aug. 5, 2022, provisional application No. 63/401,331, filed on Aug. 26, 2022, provisional application No. 63/423,161, filed on Nov. 7, 2022.

(56) References Cited

U.S. PATENT DOCUMENTS

| | | | |
|---|---|---|---|
| 6,626,965 | B2 | 9/2003 | Workman et al. |
| 6,933,326 | B1 | 8/2005 | Griffey et al. |
| 8,323,701 | B2 | 12/2012 | Daniel et al. |
| 8,357,403 | B2 | 1/2013 | Daniel et al. |
| 8,372,437 | B2 | 2/2013 | Daniel |
| 8,409,626 | B2 | 4/2013 | Daniel et al. |
| 8,858,647 | B2 | 10/2014 | Markman |
| 10,143,777 | B2 | 12/2018 | LeVaughn et al. |
| 10,898,312 | B2 | 1/2021 | Wirth et al. |
| 11,058,530 | B2 | 7/2021 | Chen et al. |
| 11,219,647 | B2 | 1/2022 | Morse et al. |
| 11,925,532 | B2 | 3/2024 | Ganey et al. |
| 2004/0260315 | A1 | 12/2004 | Dell et al. |
| 2007/0248638 | A1 | 10/2007 | Van Dyke et al. |
| 2010/0040687 | A1 | 2/2010 | Pedrozo et al. |
| 2010/0291172 | A1 | 11/2010 | Drunecky |
| 2013/0084323 | A1 | 4/2013 | Riebman et al. |
| 2013/0138222 | A1 | 5/2013 | Horton |
| 2016/0136328 | A1 | 5/2016 | LeVaughn et al. |
| 2017/0157295 | A1 | 6/2017 | Daniel |
| 2018/0043058 | A1 | 2/2018 | Kheradvar |
| 2018/0214493 | A1 | 8/2018 | Koob et al. |
| 2019/0091371 | A1 | 3/2019 | LeVaughn et al. |
| 2019/0134268 | A1 | 5/2019 | Malinin |
| 2019/0269815 | A1 | 9/2019 | Williams et al. |
| 2021/0154240 | A1 | 5/2021 | Pavesio et al. |
| 2021/0393852 | A1 | 12/2021 | McQueen et al. |
| 2024/0156642 | A1 | 5/2024 | Ganey et al. |

FOREIGN PATENT DOCUMENTS

| | | |
|---|---|---|
| WO | 9706837 A1 | 2/1997 |
| WO | 2012112417 A2 | 8/2012 |
| WO | 2021/127230 A1 | 6/2021 |

OTHER PUBLICATIONS

International Search Report (ISR) for PCT/US2023/26444 mailed Jan. 4, 2024 (4 pages).

Written Opinion (WO) for PCT/US2023/26444 mailed Jan. 4, 2024 (5 pages).

International Search Report (ISR) for PCT/US2023/026447 mailed Oct. 10, 2023 (4 pages).

Written Opinion for PCXT/US2023/026447 mailed Oct. 10, 2023 (6 pages).

Thomas J. Koob et al., "Properties of dehydrated human amnion/chorion composite grafts: Implications for wound repair soft tissue regeneration" Journal of Biomedical Materials Part B: Applied Biomaterials, vol. 102, No. 6. p. 1353-1362, Mar. 25, 2014.

John McQuilling et al., "Characterisation of dehydrated amnion chorion membranes and evaluation of fibroblast and keratinocyte responses in vitro" International Wound Journal vol. 16, No. 13, p. 827-840, Jun. 1, 2019.

Christoph Schoepf, "The Tutoplast Process: A Review Efficacy" Zimmer Dental, Jan. 1, 2008 XP 093042590, URL:http://zimmer.vilem.bg/Regenerative/lib-artTutoplastProcessSchoepf.pdf (accessed Apr. 27, 2023).

Brennan et al., The Journal of Biological Chemistry, vol. 259, No. 22, dated Nov. 25, 1984, p. 13742-13750 (Year: 1984).

Sarvari et al., Journal of Materials Science: Materials in Medicine (2022) 33:32, 26 pages (Year: 2022).

EXAMPLE 1

COMPARATIVE EXAMPLE 1 https://organogenesis.com/surgical-sports-medicine/nushield/
Accessed on August 1, 2022

COMPARATIVE EXAMPLE 2 https://www.mimedx.com/products/epifix/
Accessed on August 1, 2022

EXAMPLE 2

COMPARATIVE
EXAMPLE 3 https://www.petepetit.com/pete-petit-
professional-blog/2015/mimedx-
products-amniofix.html
Accessed on August 1, 2022

STERILE HUMAN PLACENTAL ALLOGRAFTS HAVING A PLURALITY OF SLITS, OPENINGS, AND/OR FENESTRATIONS FORMED THEREON

TECHNICAL FIELD

The present invention relates generally to the field of human placental tissues, and more particularly, to growth factor rich sterile human placental allografts and methods of making thereof in which the allografts have various dental, cosmetic, and wound healing applications. In certain aspects, the sterile human placental allografts have slits, openings, and/or fenestrations formed thereon that are configured to pass wound exudate from a wound through the sterile human placental allograft and away from the wound to facilitate wound drainage, wound healing, or a combination thereof.

BACKGROUND

The use of human placenta for medical purposes dates back to 1593, when Li Shizhen wrote about the use of "zi he chi" (human placenta) in the *Compendium of Materia Medica*. However, it was not until 1910 that the advantages of placental membranes for skin transplantation were formally documented in the medical literature.

Use of placental membranes for clinical purposes continues to date. To date, placental membrane processing has primarily focused on the preservation of cells within a tissue or removal of all non-solid components for the purpose of delivering stem cells and/or providing a substrate for regenerative growth. These placental membrane processing techniques often result in loss of endogenous growth factors found within the human placental tissue and/or result in endogenous degradative processes that further result in a loss of endogenous growth factors found in the human placental tissue thereby resulting in reduced end use efficacy (e.g., reduced wound healing) for any allografts obtain from these processes.

SUMMARY

It is an object of the invention to provide safe, biocompatible, growth factor-rich sterile human placental allografts grafts. The methods disclosed herein achieve these biocompatible, growth factor-rich sterile human placental allografts grafts while maintaining a growth factor profile that mimics the human placenta in vivo. These methods clean and prepare the human placental tissues in a gentle and effective manner, while minimizing the risk of comprising biologic tissue and/or growth factors for subsequent allograft implantation/transplantation. In particular, the disclosed methods utilize various mild cleaning, preservation, and mild sterilization techniques using cold physiological buffers, gentle handling, dehydration at ambient or physiological temperatures, and mild sterilization conditions of the human placental allografts disclosed herein to obtain sterile human placental allografts that maintain a growth factor profile that mimics the human placenta in vivo. These sterile human placental allografts have various different clinical and cosmetic purposes and may achieve, for example, improved wound healing when compared with conventional human placental allografts because of its growth factor profile. Furthermore, the allografts disclosed herein meet or exceed all requirements set by the Food and Drug Administration (FDA) and American Association of Tissue Banks (AATB).

In certain aspects, disclosed herein is a method of preparing a sterile human placental allograft comprising (a) providing a human placental tissue from a donor within 24 hours to 72 hours post-childbirth; (b) removing any visible blood, blood clots, and/or blood components from the human placental tissue without scraping or scrubbing the human placental tissue to preserve structural integrity of the human placental tissue; (c) washing the human placental tissue in an isotonic solution while maintaining the structural integrity of the human placental tissue; (d) dehydrating the human placental tissue thereby forming the dehydrated human placental tissue; (e) resizing the dehydrated human placental tissue into dehydrated human placental tissue portions having predetermined sizes; and (f) sterilizing the dehydrated human placental tissue portions of step (e) thereby forming the sterile human placental allograft.

In certain aspects, either before step (a) or during step (a) disinfecting the human placental tissue with at least one of a bactericidal composition, a tuberculocidal composition, a fungicidal composition, a virucidal composition, or any combination thereof. In certain aspects, the at least one of a bactericidal composition, tuberculocidal composition, fungicidal composition, virucidal composition, or any combination thereof includes an alcohol solution and more preferably an isopropyl alcohol at a concentration of 70% to 100%. In preferred embodiments the alcohol concentration ranges from 70% to 75%, and in most preferred embodiments, the alcohol is 70% isopropyl alcohol. Isopropyl alcohol is preferred over other commercially available lab and/or pharmaceutical grade alcohols, such as ethanol, because isopropyl alcohol advantageously disinfects and cleans the human placental tissue without damaging (e.g., unduly dehydrating, initiating apoptotic processes, and/or necrotic processes) the placental tissue. In certain aspects, predetermined volumes of the at least of a bactericidal composition, a tuberculocidal composition, a fungicidal composition, a virucidal composition, or any combination thereof may be used in which the predetermined volumes range from 250 mL to 1000 mL and more preferably 400 mL to 600 mL.

In certain aspects, step (b) comprises manual hematopoietic reduction by manually removing any visible blood, blood clots, blood components, and/or other debris from the human placental tissue.

In certain aspects, the isotonic solution comprises at least one of 1× phosphate buffered saline, isotonic saline, lactated ringers, Plasma-Lyte® (NaCl 5.26 g/L, KCl 0.37 g/L, Magnesium Chloride hexahydrate 0.30 g/L, Sodium Acetate trihydrate 3.68 g/L, Sodium Gluconate 5.02 g/L at pH 7.4), Normosol® (NaCl 5.26 g/L, KCl 0.37 g/L, Magnesium Chloride 0.30 g/L, Sodium Acetate anhydrous 2.22 g/L, Sodium Gluconate 5.02 g/L at pH 7.4), or any combination thereof.

In certain aspects, the method further comprises repeating step (c) for a predetermined number of times.

In certain aspects, each wash step (c) is at a temperature ranging from 4 to 15° C. for a time-period of from 5 minutes to 15 minutes.

In certain aspects, the dehydrating step (d) is at a temperature ranging from 20 to 40° C. for a time-period of from 60 minutes to 4.5 hours thereby resulting in a dehydrated (or dried) human placental tissue having approximately 10 to 15% residual water content. In certain preferred aspects, the dehydrating step (d) is at a temperature ranging from 30 to 40 a time-period of from 60 minutes to 4.5 hours thereby resulting in a dehydrated (or dried) human placental tissue having approximately 10 to 15% residual water content.

In certain aspects and during, for example, step (e) is re-sized into predetermined sizes of the human placental tissue portions range from 1 cm×1 cm to 8 cm×8 cm for square and rectangular shaped human placental tissue portions. In further aspects, the square and rectangular shaped human placental tissue portions may include 2 cm×2 cm, 2 cm×3 cm, 2 cm×4 cm, 4 cm×4 cm, 4 cm×6 cm, 4 cm×8 cm, 6 cm×6 cm, 8 cm×8 cm in which any endpoints within any of these ranges may serve as endpoints for any additional ranges falling therein. In certain aspects, the predetermined sizes may include round and/or circular shape human placental tissue portions having diameters ranging from 0.5 mm to 50 mm in which any endpoints within any of these ranges may serve as endpoints for any additional ranges falling therein, and in further aspects, the sizes may include round and/or circular shape human placental tissue portions having diameters of 2 mm, 4 mm, 6 mm, 8 mm, 10 mm, 12 mm, 14 mm, 16 mm, 20 mm, 30 mm, 40 mm, or 50 mm.

In certain aspects, the placental tissue portions comprise a predetermined shape and is configured for dental, cosmetic, and/or wound healing applications.

In certain aspects, the sterilizing step (f) comprises sterilizing with e-beam irradiation.

In certain aspects, step (f) comprises e-beam irradiating the dehydrated human placental tissue portions to a sterility assurance level (SAL) of $10^{-6}$, as determined by dose mapping by the E-beam vendor, to form the sterile human placental allograft.

In certain aspects, the human placental tissue comprises intact placental tissue. In this aspect, the dehydrated human placental tissue of step (d) and the dehydrated human placental tissue portions having predetermined sizes of step (e) are intact in cross-section in which a human amnion layer and a human chorion layer have an intact human intermediate spongy layer positioned there between connecting the human amnion layer to the human chorion layer. In this aspect, sterile human placental allografts of step (f) are intact in cross-section in which the human amnion layer and the human chorion layer have an intact human intermediate spongy layer positioned there between connecting the human amnion layer to the human chorion layer.

In certain aspects, the sterile human placental allograft produced by, for example, the above method is configured for dental, cosmetic, and/or wound healing applications.

Moreover, in certain aspects before step (f) (preferably after step (d) and after step (e), or after step (d) and before step (e)), slits, openings, and/or fenestrations are formed on (and through) the human placental allograft and/or in the dehydrated human placental portions of such that the sterile human placental allograft (of step (f)) includes a plurality of slits, openings, or fenestrations (e.g., flaps) formed on an upper surface of the allograft and having corresponding slits (e.g., aligned and/or axially aligned), openings or fenestrations (flaps) formed on a lower surface of the allograft such that the slits, openings, or fenestrations (e.g., flaps) formed on the upper surface of the allograft are in fluid communication with the corresponding slits, openings, or fenestration (e.g., flaps) formed on the lower surface of the allograft such that, when in use, the allografts allow wound exudate to flow from a wound and pass through the allograft in a direction from a lower surface of the allograft away from the wound to the upper surface of the allograft thereby facilitating wound drainage, wound healing, or a combination thereof. In certain aspects, the human sterile placental allograft comprises a plurality of fenestrations formed on the sterile human placental allograft that are configured for wound exudate to flow from a wound and pass through the sterile human placental allograft in a direction from the lower surface of the sterile human placental allograft to the upper surface of the sterile human placental allograft to facilitate wound drainage, wound healing, or a combination thereof. In this aspect, each fenestration is a flap that is configured to open when wound exudate and/or other bodily fluids originating from a wound flow through the sterile human placental allograft and to close when no wound exudate and/or other bodily fluids are flowing through the sterile human placental allograft. When in use and in an open configuration, the flap moves in a direction away from the lower surface and the upper surface of the sterile human placental allograft. In certain aspects, the fenestration has a predetermined shape, which includes a "V" shape, a "U" shape, a semi-"U" shape, a semi-square shape, a semi-rectangular shape, or combinations thereof.

Also disclosed herein are sterile human placental allografts. In certain aspects, these sterile human placental allografts are produced by the methods disclosed herein. The sterile human placental allografts disclosed herein are preferably non-immunogenic—resulting in little or no immune response post-implantation/transplantation into a human recipient.

In certain aspects, the sterile human placental allograft comprises at least two of the following: (a) interleukin-1 receptor antagonist (IL-1ra) ranging from 200 to 7800 pg/cm$^2$; (b) hepatocyte growth factor (HGF) ranging from 500 to 8500 pg/cm$^2$; (c) vascular endothelial growth factor receptor 1 (VEGFR1) ranging from 800 to 2750 pg/cm$^2$; (d) hyaluronic acid (HA) ranging from $5.0 \times 10^6$ to $1.5 \times 10^8$ pg/cm$^2$; (e) platelet derived growth factor subunit B homodimer (PDGF-BB) ranging from 150 to 400 pg/cm$^2$; (f) glycosaminoglycans (GAGs); (g) collagen, and (h) exosomes in which any endpoints within any of the above-mentioned ranges may serve as endpoints for any additional ranges falling therein. In this aspect, the sterile human placental allograft is intact in cross-section in which the human amnion layer and the human chorion layer have an intact human intermediate spongy layer positioned there between connecting the human amnion layer to the human chorion layer. In certain aspects, the human placental allograft may include at least three, at least four, at least five, at least six, at least seven, or at least eight of the following: (a) interleukin-1 receptor antagonist (IL-1ra) ranging from 200 to 7800 pg/cm$^2$; (b) hepatocyte growth factor (HGF) ranging from 500 to 8500 pg/cm$^2$; (c) vascular endothelial growth factor receptor 1 (VEGFR1) ranging from 800 to 2750 pg/cm$^2$; (d) hyaluronic acid (HA) ranging from $5.0 \times 10^6$ to $1.5 \times 10^8$ pg/cm$^2$; (e) platelet derived growth factor subunit B homodimer (PDGF-BB) ranging from 150 to 400 pg/cm$^2$; (f) glycosaminoglycans (GAGs); (g) collagen, and (h) exosomes in which any endpoints within any of the above-mentioned ranges may serve as endpoints for any additional ranges falling therein. In this aspect, the sterile human placental allograft is intact in cross-section in which the human amnion layer and the human chorion layer have an intact human intermediate spongy layer positioned there between connecting the human amnion layer to the human chorion layer.

In certain aspects, the sterile human placental allograft is configured for dental, cosmetic, and/or wound healing applications.

In certain aspects, the sterile human placental allograft comprises a predetermined size of 1 cm×1 cm to 8 cm×8 cm for square and rectangular shaped sterile human placental allografts. In further aspects, the square and rectangular shaped sterile human placental allografts may include 2 cm×2 cm, 2 cm×3 cm, 2 cm×4 cm, 4 cm×4 cm, 4 cm×6 cm, 4 cm×8 cm, 6 cm×6 cm, 8 cm×8 cm in which any endpoints within any of these ranges may serve as endpoints for any additional ranges falling therein. In certain aspects, the predetermined sizes may include round and/or circular shaped sterile human placental allografts having diameters ranging from 0.5 mm to 50 mm in which any endpoints within any of these ranges may serve as endpoints for any additional ranges falling therein, and in further aspects, the sizes may include round and/or circular shaped sterile human placental tissue portions having diameters of 2 mm, 4 mm, 6 mm, 8 mm, 10 mm, 12 mm, 14 mm, 16 mm, 20 mm, 30 mm, 40 mm, or 50 mm.

In certain aspects, the sterile human placental allograft comprises a circular shape, a square shape, a rectangular shape, an ovoid shape, a triangular shape, or any combination thereof.

In certain aspects, an upper and/or lower surface of the sterile human placental allograft is planar.

In certain aspects, the upper and lower surfaces of the sterile human placental allograft are planar.

In certain aspects, the sterile human placental allograft includes a plurality of slits, openings, or fenestrations (e.g., flaps) formed on an upper surface of the allograft and further includes corresponding slits, openings or fenestrations (flaps) formed on a lower surface of the allograft such that the slits, openings, or fenestrations (e.g., flaps) formed on the upper surface of the allograft are in fluid communication with the corresponding slits, openings, or fenestration (e.g., flaps) formed on the lower surface of the allograft such that, when in use, the allografts allow wound exudate to flow away from a wound and pass through the allograft in a direction from a lower surface of the allograft to the upper surface of the allograft thereby facilitating wound drainage, wound healing, or a combination thereof. In certain aspects, the human sterile placental allograft comprises a plurality of fenestrations formed on the sterile human placental allograft that are configured for wound exudate to flow from a wound and pass through the sterile human placental allograft in a direction from the lower surface of the sterile human placental allograft to the upper surface of the sterile human placental allograft to facilitate wound drainage, wound healing, or a combination thereof. In this aspect, each fenestration is a flap that is configured to open when wound exudate and/or other bodily fluids are flowing from a wound through the sterile human placental allograft and to close when no wound exudate and/or other bodily fluids are flowing through the sterile human placental allograft. When in use and while exudate is flowing through the allograft, the flap moves in a direction away from the lower surface and the upper surface of the sterile human placental allograft when open. In certain aspects, the fenestration has a predetermined shape, which includes a "V" shape, a "U" shape, a semi-"U" shape, a semi-square shape, a semi-rectangular shape, or combinations thereof.

In certain aspects, the sterile human placental allograft consists essentially of the human amnion membrane, and in further aspects, the sterile human placental allograft consists of the human amnion membrane. In each of these aspects, the sterile human placental allograft (consisting essentially of and/or consisting of the amnion membrane) includes at least two of the following: (a) interleukin-1 receptor antagonist (IL-1ra) ranging from 150 to 1800 pg/cm$^2$; (b) hepatocyte growth factor (HGF) ranging from 75 to 400 pg/cm$^2$; (c) vascular endothelial growth factor receptor 1 (VEGFR1) ranging from 50 to 250 pg/cm$^2$; (d) hyaluronic acid (HA) ranging from $1.1 \times 10^6$ to $2.0 \times 10^7$ pg/cm$^2$; (e) platelet derived growth factor subunit B homodimer (PDGF-BB) ranging from 200 to 500 pg/cm$^2$; (f) glycosaminoglycans (GAGs); (g) collagen, and (h) exosomes in which any endpoints within any of the above-mentioned ranges may serve as endpoints for any additional ranges falling therein. In this aspect, the sterile human placental allograft is configured for dental, cosmetic, and/or wound healing applications. In this aspect, the sterile human placental allograft comprises a predetermined size of ranging from 1 cm×1 cm to 8 cm×8 cm for rectangular and/or square shaped human placental allografts in which any endpoints within any of these ranges may serve as endpoints for any additional ranges falling therein and ranging from 2 mm diameter to 50 mm diameter for circular and/or round sterile human placental allografts in which any endpoints within any of these ranges may serve as endpoints for any additional ranges falling therein. In this aspect, the sterile human placental allograft comprises a circular shape, a square shape, a rectangular shape, an ovoid shape, a triangular shape, or any combination thereof. In this aspect, an upper and/or lower surface of the sterile human placental allograft is planar. In this aspect, the upper and lower surfaces of the sterile human placental allograft are planar.

Also disclosed herein are kits comprising the sterile human placental allograft packaged in a sterile container. In this aspect, the sterile human placental allograft is produced by the methods disclosed herein.

Embodiments of the invention can include one or more or any combination of the above features and configurations.

Additional features, aspects and advantages of the invention will be set forth in the detailed description which follows, and in part will be readily apparent to those skilled in the art from that description or recognized by practicing the invention as described herein. It is to be understood that both the foregoing general description and the following detailed description present various embodiments of the invention, and are intended to provide an overview or framework for understanding the nature and character of the invention as it is claimed. The accompanying drawings are included to provide a further understanding of the invention, and are incorporated in and constitute a part of this specification.

BRIEF DESCRIPTION OF THE DRAWINGS

These and other features, aspects and advantages of the present invention are better understood when the following detailed description of the invention is read with reference to the accompanying drawings, in which:

FIG. 2A shows hematoxylin and eosin stain for structure; FIG. 2B shows alcian blue staining for glycosaminoglycans; FIG. 2C shows Van Gieson staining for elastin and collagen; FIG. 2D shows staining for collagen I in brown; FIG. 2E shows staining for collagen III in brown; and FIG. 2F shows staining for fibronectin in brown;

FIG. 3A shows hematoxylin and eosin stain for structure; FIG. 3B shows alcian blue staining for glycosaminoglycans; FIG. 3C shows Van Gieson staining for elastin and collagen; FIG. 3D shows staining for collagen I in brown; FIG. 3E shows staining for collagen III in brown; and FIG. 3F shows staining for fibronectin in brown;

DETAILED DESCRIPTION

Figure 1:
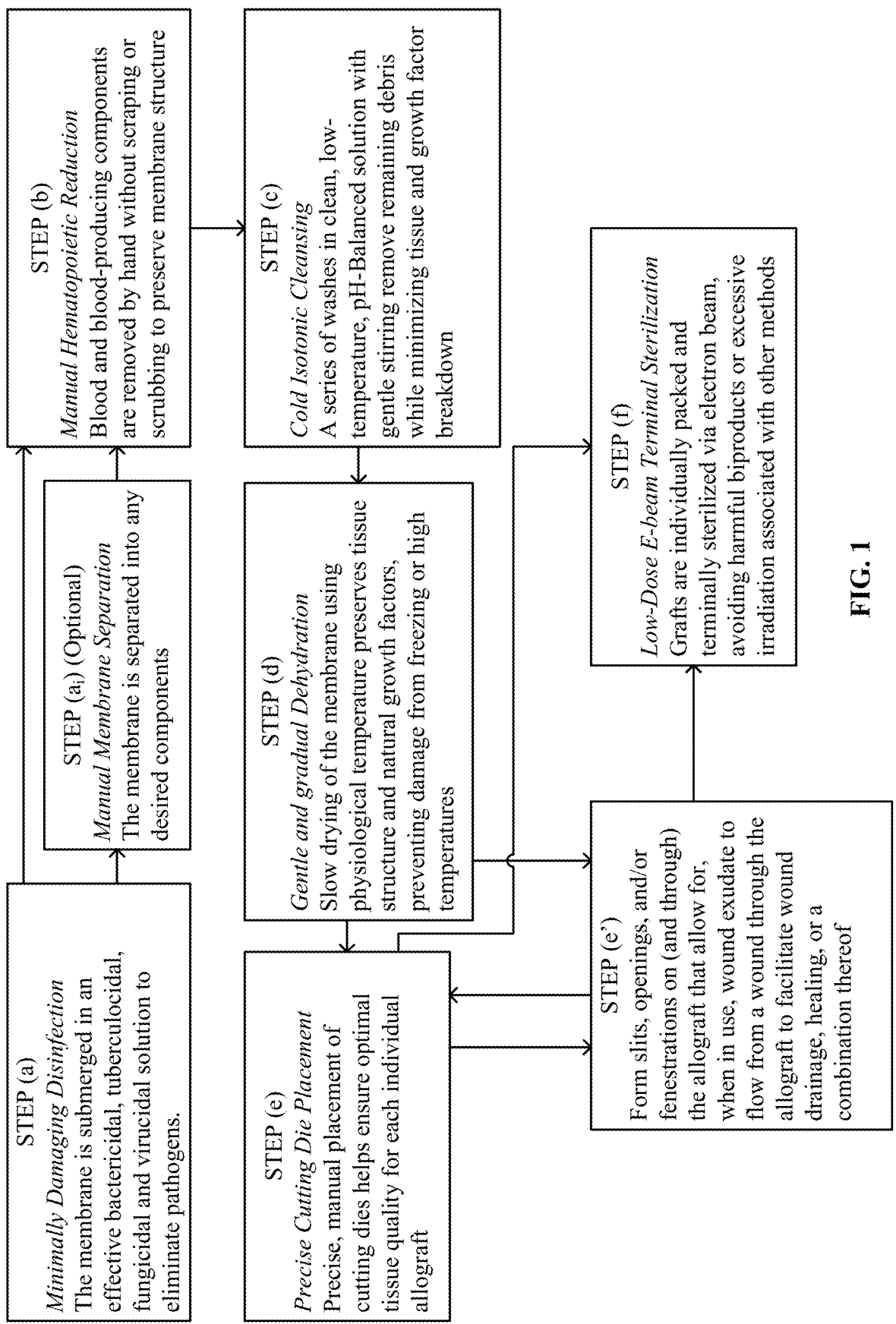
FIG. 1 schematically depicts the steps in the method of making the sterilized human placental allografts disclosed herein.
Figure 2A:
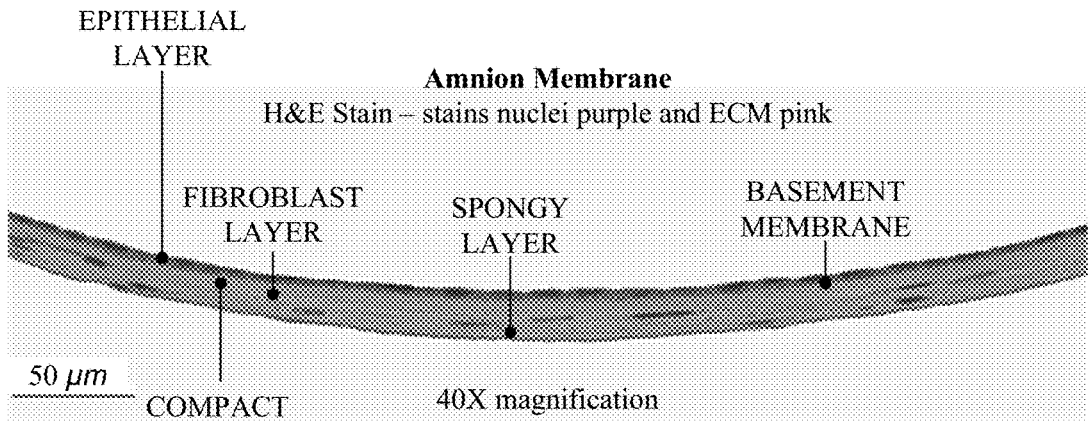
FIGS. 2A, 2B, 2C, 2D, 2E, and 2F each show microscopic images depicting the histology of the dehydrated amnion stroma (i.e., the sterile human placental allograft according to one embodiment) obtained from the methods disclosed herein.
Figure 2B:
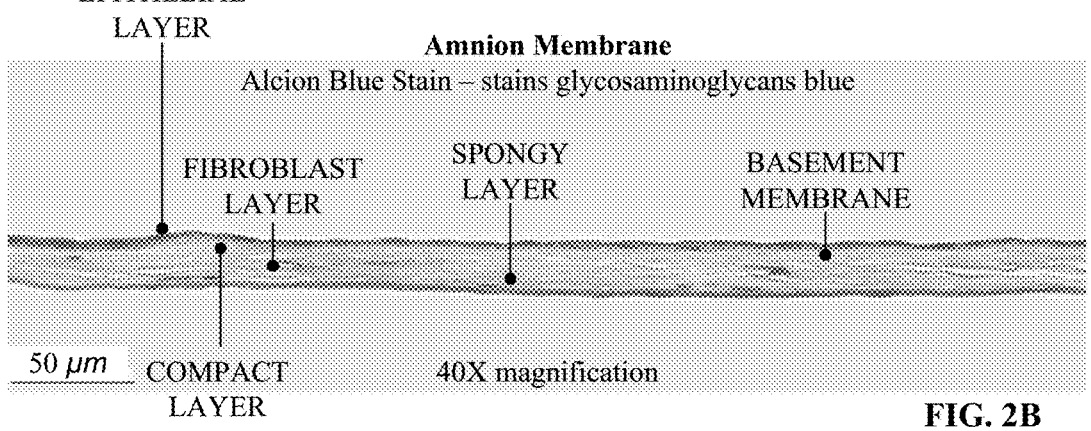
Figure 2C:
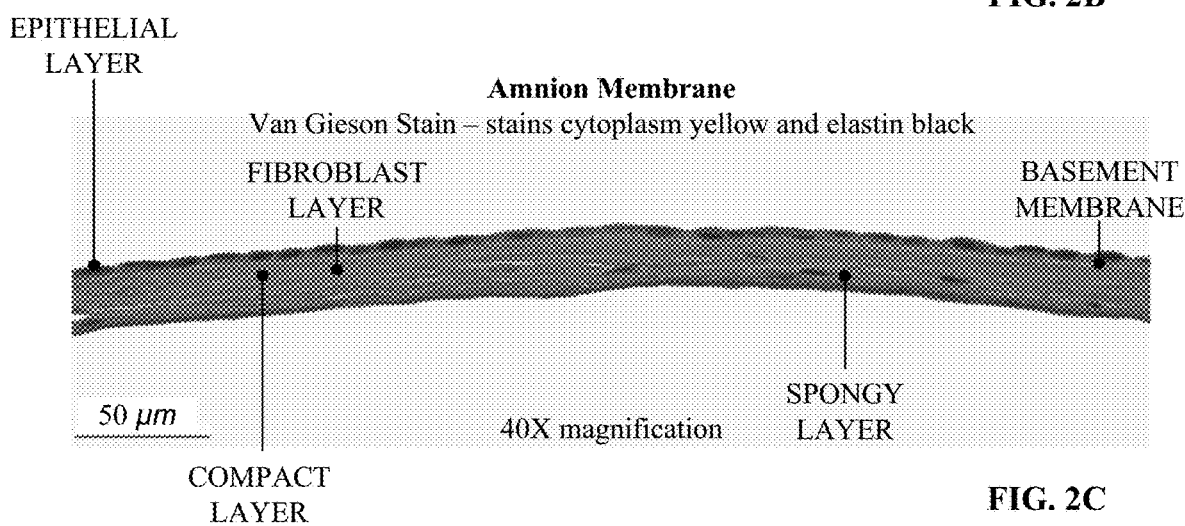
Figure 2D:
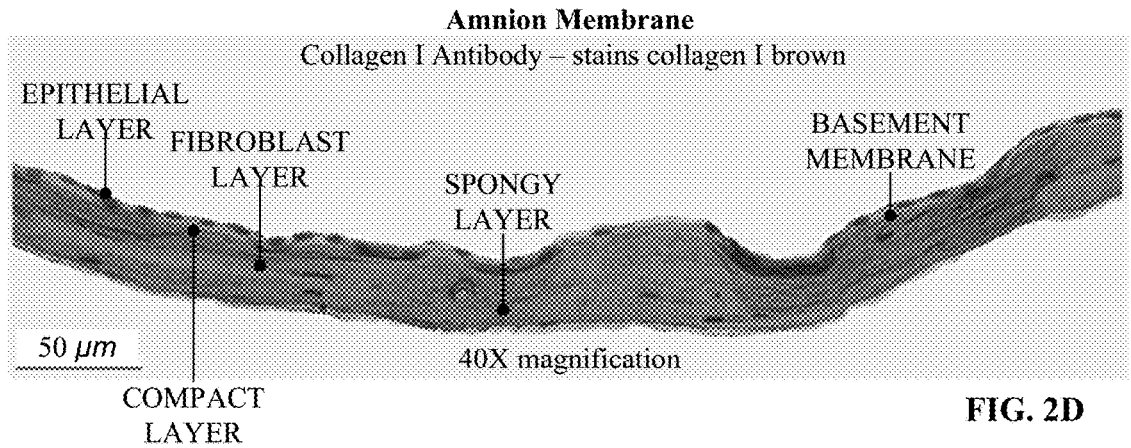
Figure 2E:
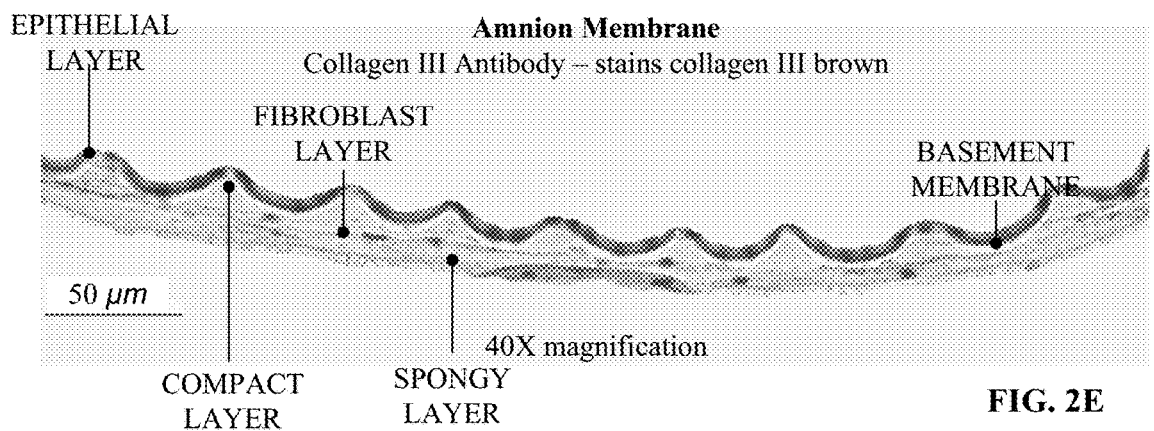
Figure 2F:
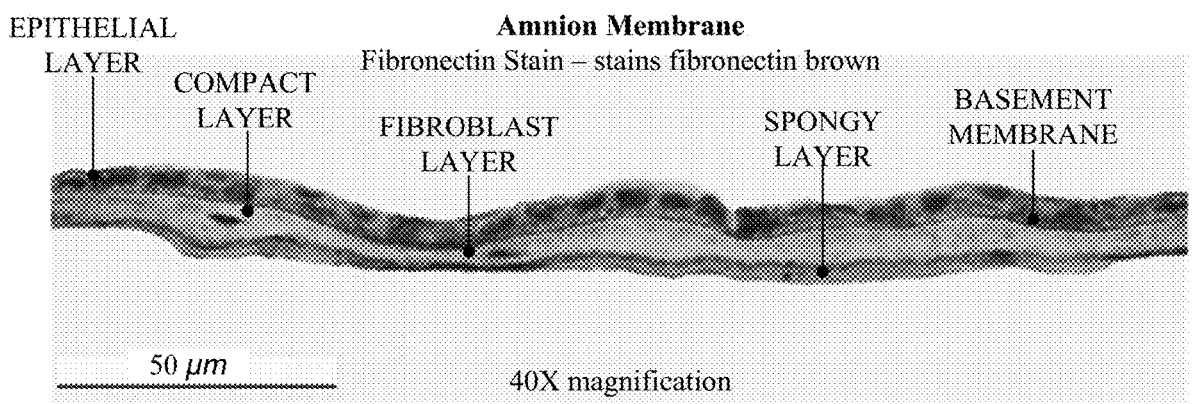
Figure 3A:
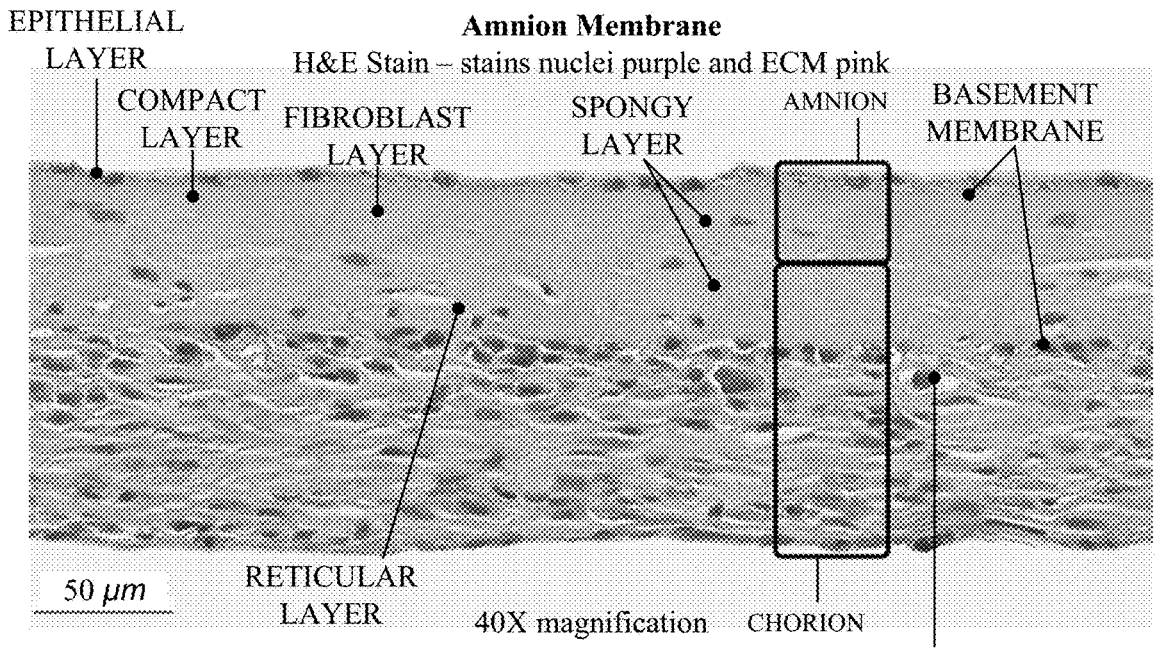
FIGS. 3A, 3B, 3C, 3D, 3E, and 3F each shown microscopic images depicting the histology of the dehydrated amnion/chorion stroma (i.e., the sterile human placental allograft according to another embodiment) obtained from the methods disclosed herein.
Figure 3B:
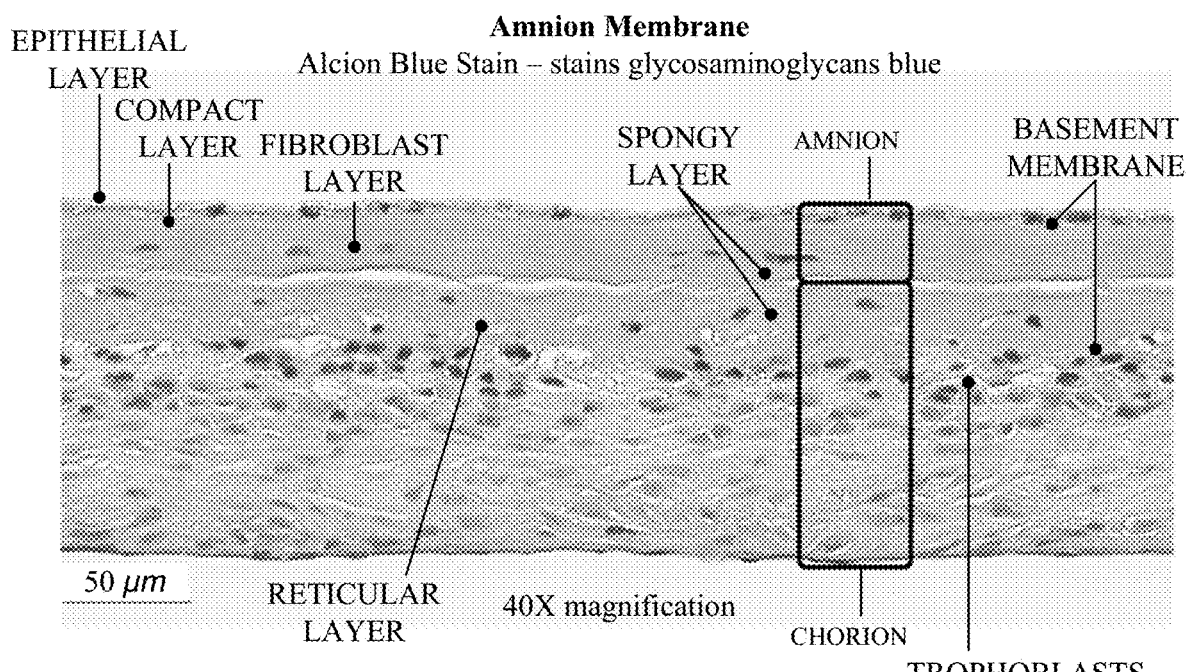
Figure 3C:
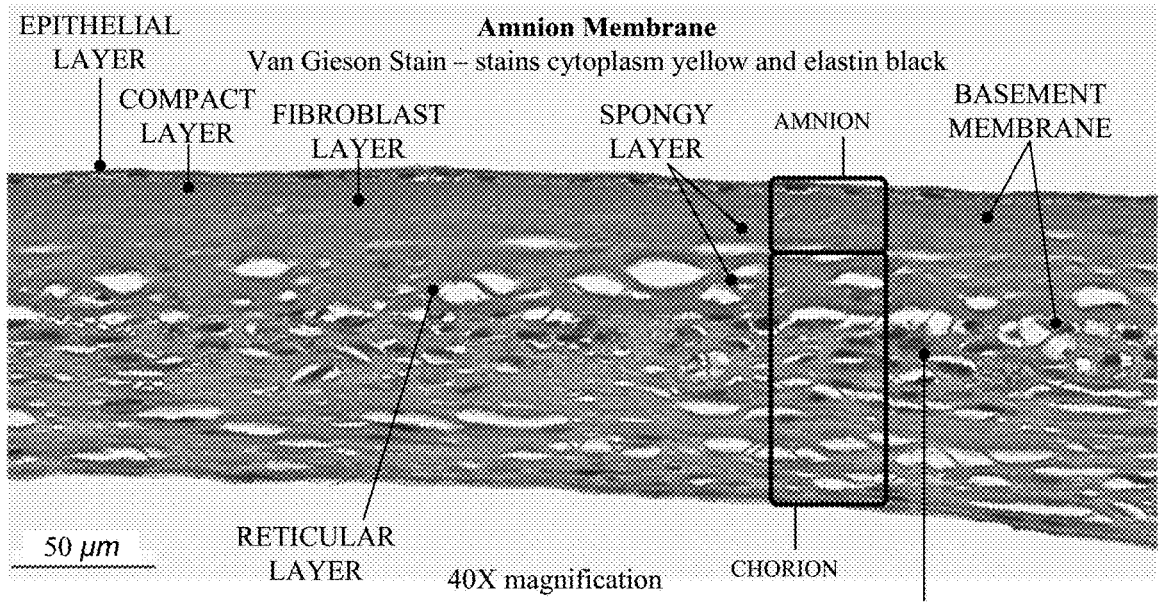
Figure 3D:
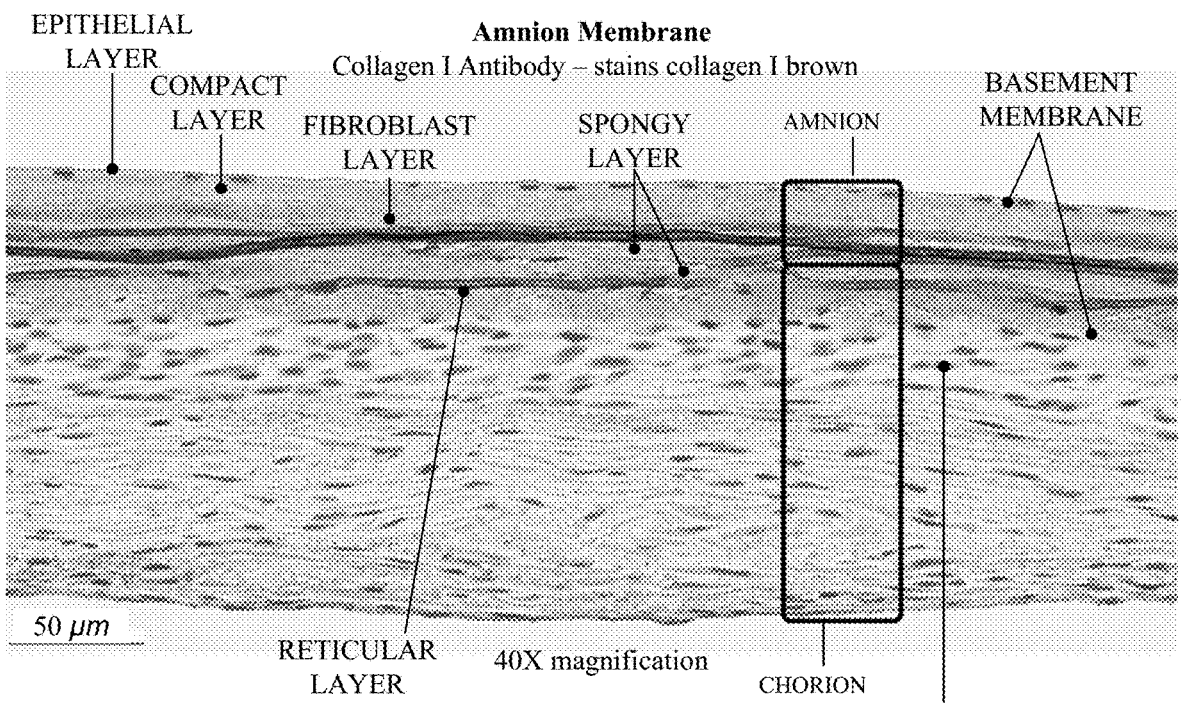
Figure 3E:
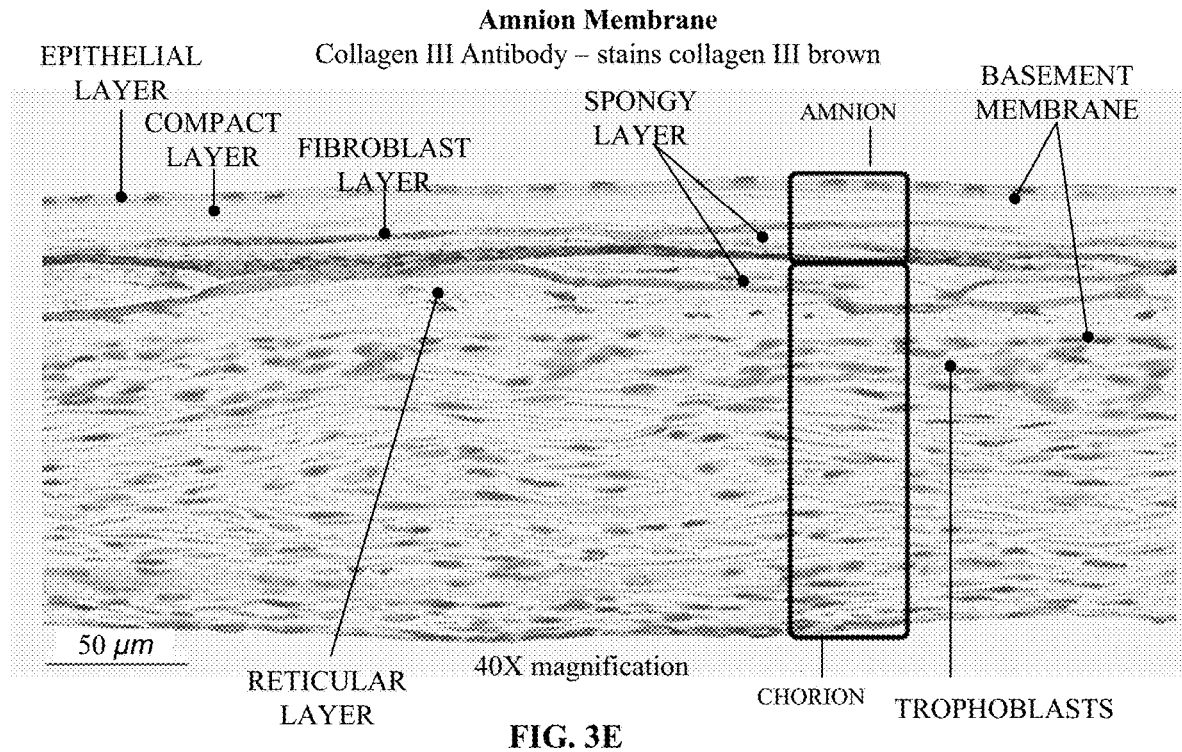
Figure 3F:
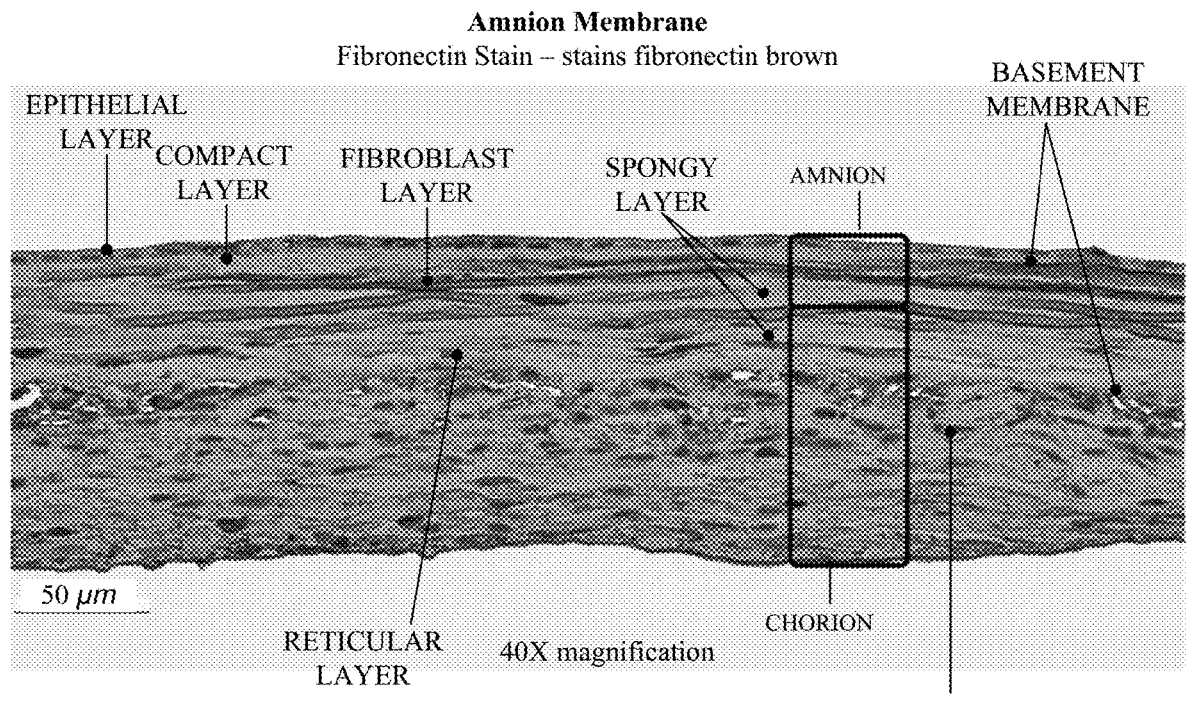
Figure 4A:
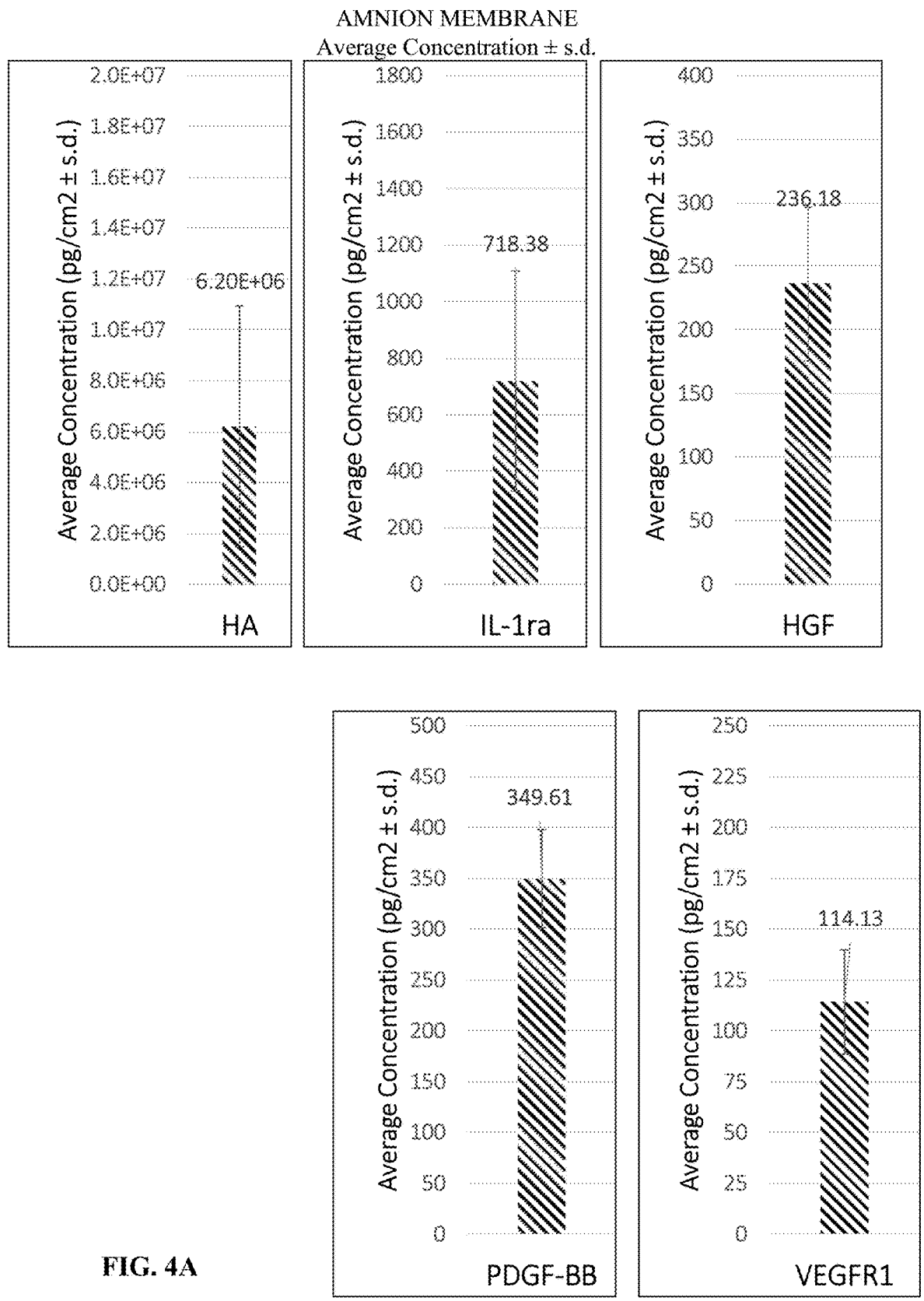
FIG. 4A are graphs depicting the growth factor elution profile for hyaluronic acid, interleukin-1 receptor antagonist (IL-1ra), hepatocyte growth factor (HGF), platelet derived growth factor subunit B homodimer (PDGF-BB), and vascular endothelial growth factor receptor 1 (VEGFR1) in the sterile human placental allograft consisting essentially of dehydrated, sterilized amnion membranes, and FIG. 4B are graphs depicting the operable and preferred ranges for the growth factor profile for hyaluronic acid, interleukin-1 receptor antagonist (IL-1ra), hepatocyte growth factor (HGF), platelet derived growth factor subunit B homodimer (PDGF-BB), and vascular endothelial growth factor receptor 1 (VEGFR1) in the sterile human placental allograft consisting essentially of dehydrated, sterilized amnion membranes.
Figure 4B:
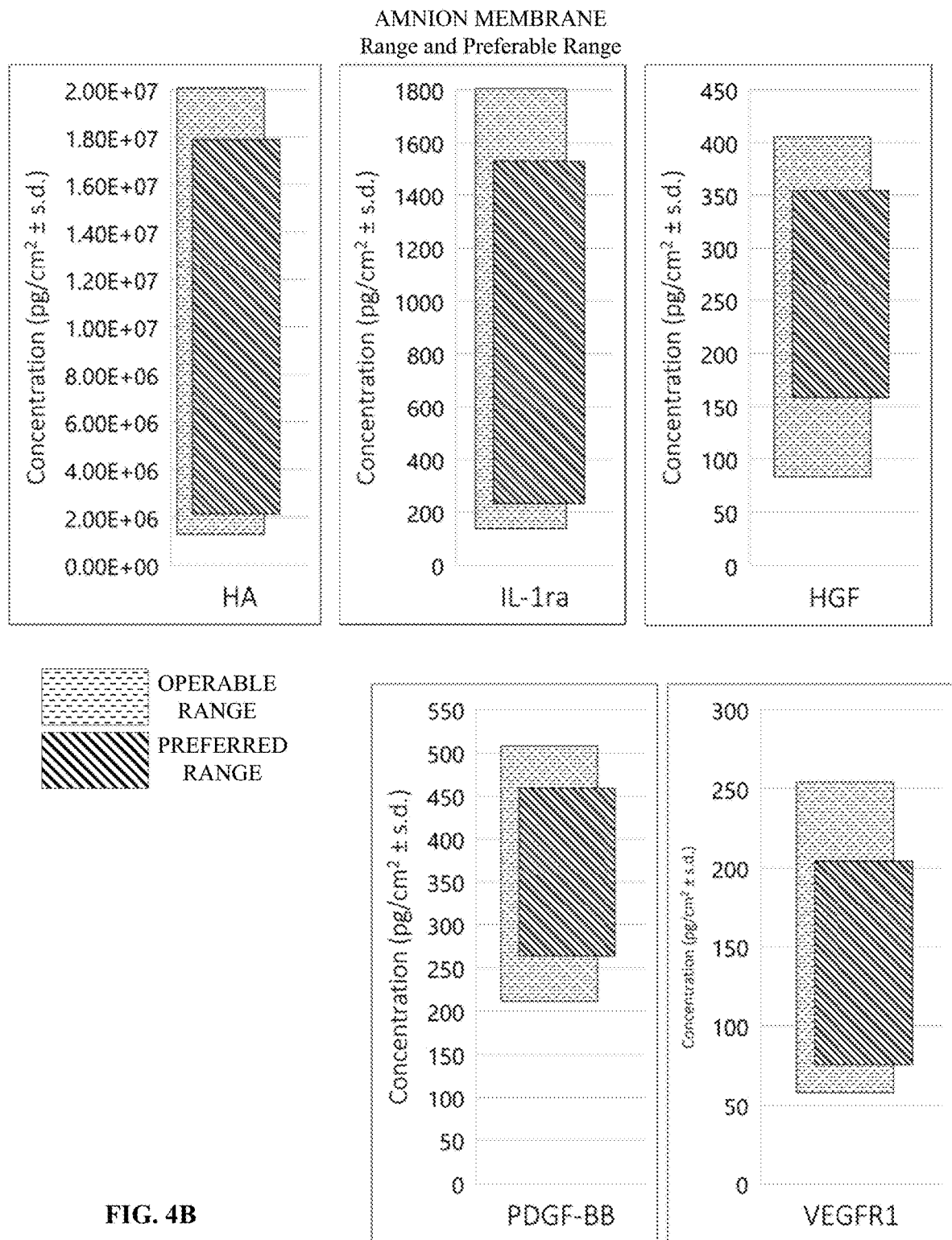
Figure 5A:
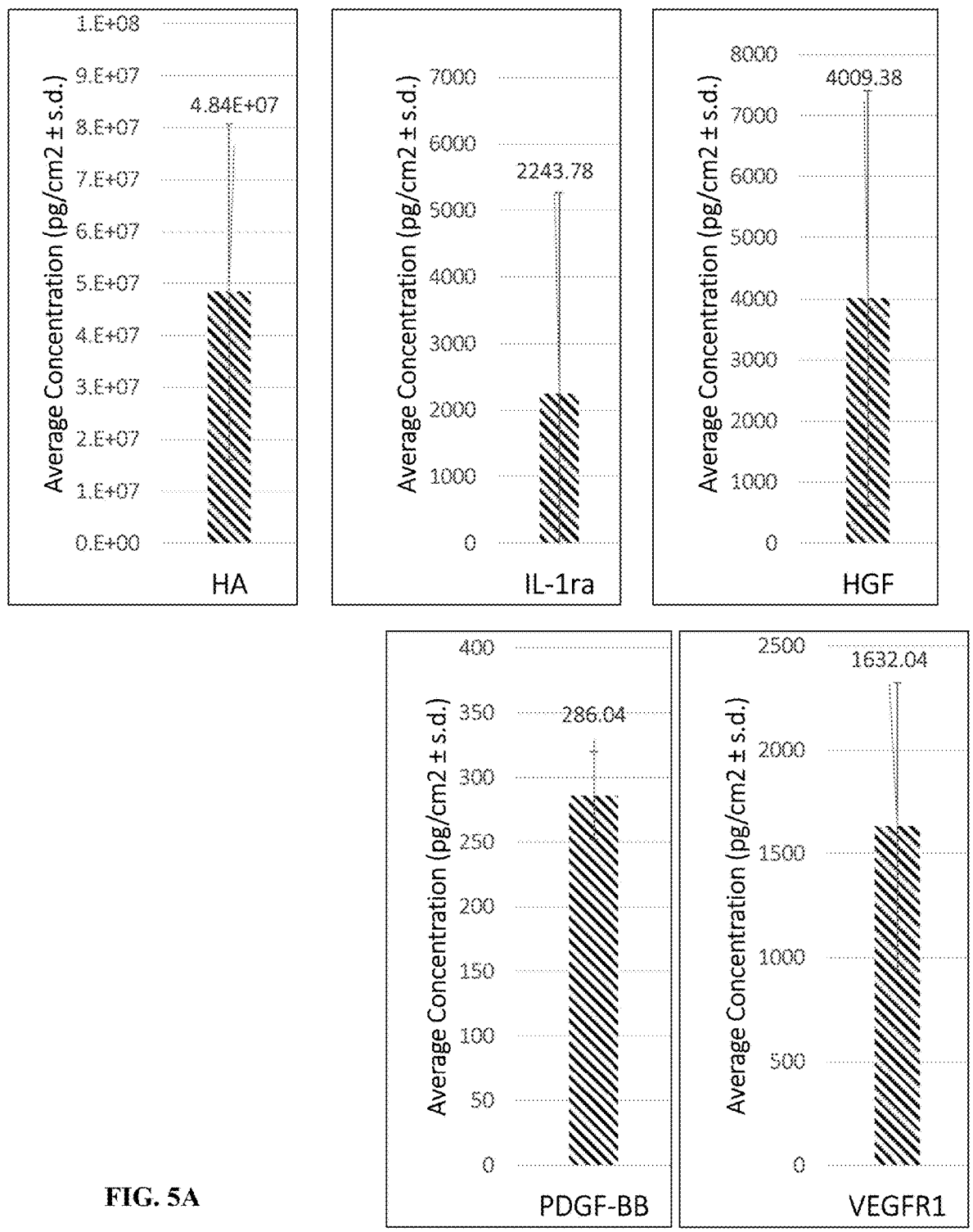
FIG. 5A are graphs depicting the growth factor elution profile for hyaluronic acid, interleukin-1 receptor antagonist (IL-1ra), hepatocyte growth factor (HGF), platelet derived growth factor subunit B homodimer (PDGF-BB), and vascular endothelial growth factor receptor 1 (VEGFR1) in the sterile human placental allograft having dehydrated, sterilized amnion/chorion membranes having an intact intermediate spongy layer in cross-section, and FIG. 5B are graphs depicting the operable ranges and preferable ranges for growth factor profile for hyaluronic acid, interleukin-1 receptor antagonist (IL-1ra), hepatocyte growth factor (HGF), platelet derived growth factor subunit B homodimer (PDGF-BB), and vascular endothelial growth factor receptor 1 (VEGFR1) in the sterile human placental allograft having dehydrated, sterilized amnion/chorion membranes.
Figure 5B:
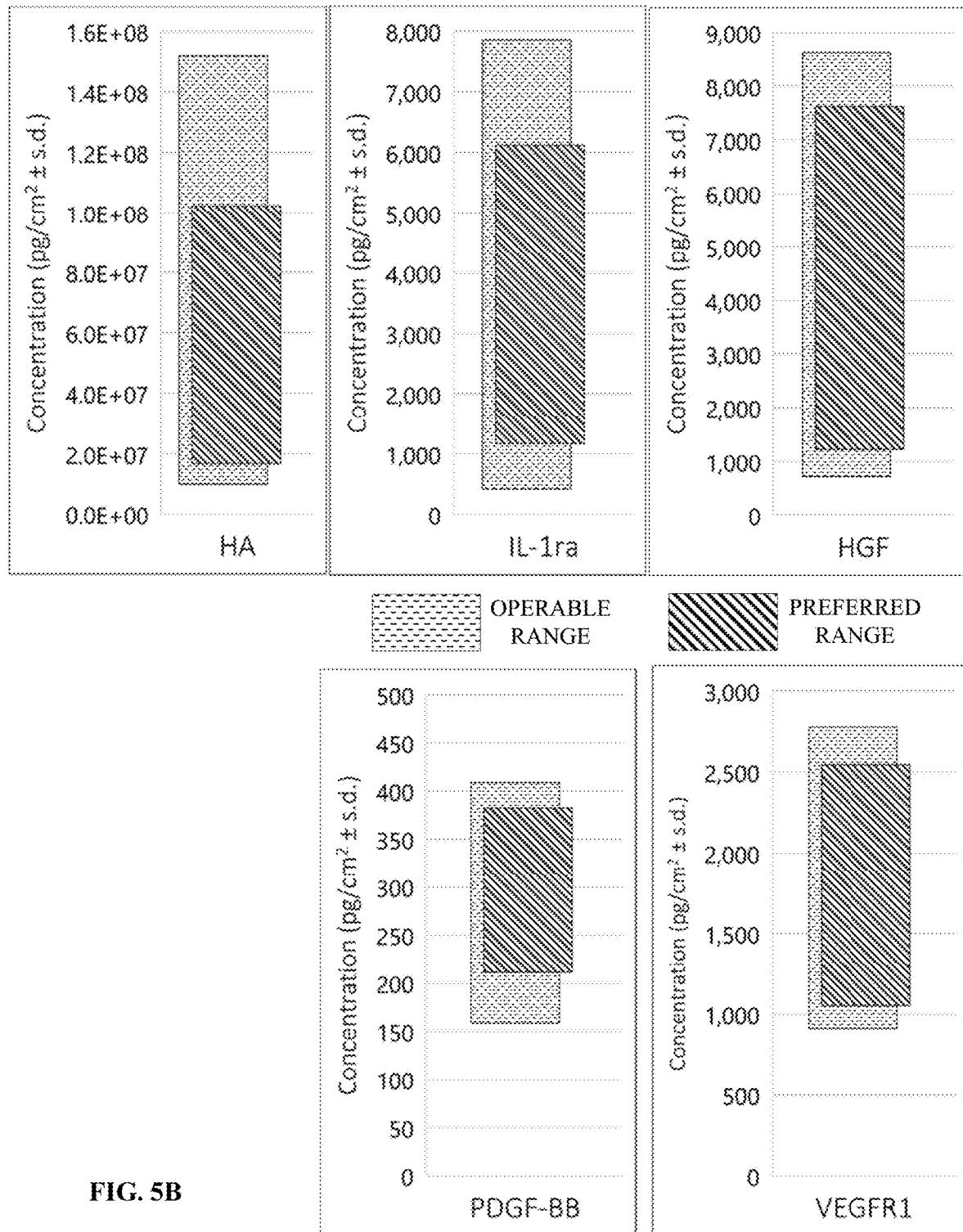

The present invention will now be described more fully hereinafter with reference to the accompanying drawings in which exemplary embodiments of the invention are shown. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention.

It must be noted that, as used in the specification and the appended claims, the singular forms "a", "an", and "the" include plural referents unless the context clearly dictates otherwise.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within the ranges as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. as well as 1, 2, 3, 4, and 5, individually. The same principle applies to ranges reciting only one numerical value as a minimum or a maximum. Furthermore, such an interpretation should apply regardless of the breadth of the range or the characteristics being described.

"Standardization" as referred to herein allows for an accurate determination of growth factors and components within the disclosed compositions for subsequent use and treatment(s) (e.g., wound healing treatments) in subjects in need thereof. Applicant has determined the range of delivered factors per $cm^2$ as delivered to the patient (subject in need thereof). What this means is that the amount of IL-1ra, HGF, VEGFR1, HA, etc. delivered to the patient/subject in need thereof is measured as the amount eluted from 1 $cm^2$ of the sterile human placental allograft. The quantification process used for standardization of the disclosed sterile human placental allograft is used to accurately reflect the relationship between human placental allograft and the growth factors and other chemical components therein. The standardization calculation is determined from the equation:

$$\frac{\text{factor assayed (pg/ml)} \cdot \text{ml of buffer}}{cm^2 \text{ of sample}} = \text{pg of factor per } cm^2$$

This is accomplished by taking a sample with a known $cm^2$ (biopsy punch preferred). The sample/punch is placed in buffer for 48-72 hours, 37° C. The contents are collected and assayed for the desired components. The results are multiplied by the amount of buffer collected. This number is divided by the $cm^2$ of the sample/punch. This can be utilized for any volume of eluate used and any sample size. The testing presented in this invention utilized a 10 mm biopsy punch (78.54 $cm^2$) in a buffered solution (1×PBS) at 37° C. for 72 hours, mimicking the application of the sterile human placental allograft in a wound space, internal or external. The eluate was collected and analyzed, mimicking what was eluted from the sterile human placental allograft to the wound. This results in a controlled and relatable amount of the sterile human placental allograft that has been tested, yielding a controlled, relatable, and quantifiable amount of growth factors and stromal components.

The phrases "human placental tissue" and "placental tissue" are used interchangeably herein to indicate human placental tissue. Unless otherwise explicitly stated herein, "human placental tissue" and "placental tissue" refer to either the completely intact human placenta (having a human umbilical cord, human amnion, human chorion, and intact human intermediate spongy layer positioned between and connecting the human amnion layer and human chorion layer) or intact human placenta tissue (i.e., only including human amnion, human chorion, and intact human intermediate spongy layer) in cross-section in which a human amnion layer and a human chorion layer have an intact human intermediate spongy layer positioned there between connecting the human amnion layer to the human chorion layer. In certain explicitly stated instances herein, "human placental tissue" and/or placental tissue consists essentially of or only consist of the human amnion that is separated from all other placental tissues. Likewise, unless explicitly stated otherwise, "sterile human placental allograft" refers allografts having intact human placenta tissue in cross-section (i.e., only including human amnion, human chorion, and intact human intermediate spongy layer) in which a human amnion layer and a human chorion layer have an intact human intermediate spongy layer positioned there between connecting the human amnion layer to the human chorion layer. In the explicitly stated instances herein, "sterile human placental allograft" refers to an allograft consisting essentially of or only consist of the human amnion that is separated from all other placental tissues.

Disclosed herein are safe, biocompatible, growth factor-rich sterile human placental allografts and methods of preparing/producing the same. The allografts and methods disclosed herein achieve these biocompatible, growth factor-rich sterile human placental allografts grafts while maintaining a growth factor profile that mimics the human placenta in vivo and that is improved compared to conventional allografts thereby achieving better therapeutic outcomes for dental applications and wound healing.

Preparation of Sterilized Human Placental Allograft

As alluded to above, it is an object to prepare sterile human placental allografts that maintain a growth factor profile that mimics the human placenta in vivo. The methods disclosed herein utilize mild conditions to ensure that various endogenous growth factors in the human placental tissue including, but not limited to, IL-1ra, HGF, VEGFR1, HA, PDGF-BB, GAGs, and collagen are preserved (and/or loss thereof is minimized) in the end resulting sterile human placental allografts disclosed herein. As generally shown in FIG. 1, the disclosed methods clean and prepare the human placental tissues in a gentle and effective manner, while minimizing the risk involved of compromising the biologic tissue for subsequent allograft implantation/transplantation. In particular and as disclosed in detail further below, the disclosed methods utilize various mild cleaning, preservation, and mild sterilization techniques using cold physiological buffers, gentle handling, dehydration at ambient or physiological temperatures, and mild sterilization conditions of the human placental allografts disclosed herein to obtain sterile human placental allografts that maintain a growth factor profile that mimics the human placenta in vivo. These sterile human placental allografts have various different clinical and cosmetic purposes and may achieve, for example, improved wound healing when compared with conventional human placental allografts. Furthermore, the allografts disclosed herein meet or exceed all requirements set by the Food and Drug Administration (FDA) and American Association of Tissue Banks (AATB).

In view of FIG. 1 and before subjecting the human placental tissue to step (a) of FIG. 1, all human placental tissue goes through a donor pre-screening and screening process. Donor pre-screening includes screening the donor's medical and social history, interviewing the donor, and physically examining the donor to eliminate high-risk donors from the potential donor pool. Either during pre-screening process or after concluding the pre-screening process, cultures of the donor's tissue and donor blood specimens are collected for comprehensive serological testing, which are subsequently performed in FDA registered and CLIA certified laboratories to further determine viability of the human donor's placental tissue for the method disclosed herein. Serological testing includes screening the donor and/or human placental tissue for the following transmissible diseases:

Hepatitis:
Hepatitis-B Surface Antigen
Hepatitis-B Core Antibody
Antibodies to the Hepatitis-C Virus
Hepatitis-B Nucleic Acid Test
Hepatitis-C Nucleic Acid Test
Human Immunodeficiency Virus
(HIV):
Antibodies to HIV-1
Antibodies to HIV-2

HIV Nucleic Acid Test
Syphilis—Rapid Plasma Reagin
Leukemia/Lymphoma
Antibodies to Human T-Lymphotropic Virus 1
Antibodies to Human T-Lymphotropic Virus 2
West Nile Virus In addition to the above serological testing and before subjecting the human placental tissue to step (a) of FIG. 1, bioburden samples are collected to evaluate the number of viable microorganisms on or in the human placental tissue. In addition, environmental monitoring samples are collected throughout to evaluate the quality of surfaces and air. The above-mentioned collections ensure that the human placental tissue and processing thereafter meet consistent microbiological control(s).

FIG. 1 schematically depicts the method of preparing a sterile human placental allograft. The method includes (a) providing a human placental tissue from a donor within 24 hours to 72 hours post-childbirth; optionally ($a_i$) separating desired components (amnion, chorion, amnion/chorion together, umbilical cord, etc) from the placenta, (b) removing any visible blood, blood clots, blood components, and/or debris from the human placental tissue without scraping or scrubbing the human placental tissue to preserve structural integrity of the human placental tissue; (c) washing the human placental tissue in an isotonic solution while maintaining the structural integrity of the human placental tissue; (d) dehydrating the human placental tissue thereby forming the dehydrated human placental tissue; (e) resizing the dehydrated human placental tissue into dehydrated human placental tissue portions having predetermined sizes; and (f) sterilizing the dehydrated human placental tissue portions of step (e) thereby forming the sterile human placental allograft.

After obtaining the human placental tissue from the donor, the human placental tissue is disinfected during step (a). In particular, the human placental tissue is placed into a bactericidal, tuberculocidal, fungicidal, and/or virucidal composition. In particular, the human placental tissue is placed into 250 mL to 1000 mL (500 ml preferred) of an alcohol solution to rinse away any extraneous non-placental components and/or any other potential contaminants. The alcohol solution preferably is isopropyl alcohol at a concentration of 70% to 100%. In preferred embodiments the alcohol concentration ranges from 70% to 75%, and in most preferred embodiments, the alcohol is 70% isopropyl alcohol. Isopropyl alcohol is preferred over other commercially available lab and/or pharmaceutical grade alcohols, such as ethanol, because isopropyl alcohol advantageously disinfects and cleans the human placental tissue without damaging (e.g., unduly dehydrating, initiating apoptotic processes, and/or necrotic processes) the placental tissue for 60 seconds to 120 seconds (90 seconds preferred) at 4° C. to 20° C. thereby reducing and/or eliminating the presence of microbes, fungi, and viruses (preferably any pathogenic microbes, fungi, and/or viruses if present) on the surface and/or within the human placental tissues. Step (a) uses minimally damaging bactericidal, tuberculocidal, fungicidal and virucidal disinfection in which the placental tissue is placed into an effective and minimally damaging disinfectant for the required time to gently reduce and/or eliminate any external contamination including, but not limited to, mycobacteria, fungi and many viruses, including herpes, HIV, Influenza, Hepatitis B and C, Ebola and SARS.

After step (a), the disinfected human placental tissue from step (a) undergoes step (b) in which the disinfected human placental tissue is visually inspected and any visible blood, blood clots, blood components, and/or undesirable debris are removed without scraping or scrubbing the human placental tissue in order to preserve structural integrity of the human placental tissue as well as the endogenous growth factors therein. In certain preferred aspects, step (b) of FIG. 1 is a manual hematopoietic reduction step in which forceps and/or tweezers, soft wet gauze and scalpels are used to remove any visible blood, blood clots, blood components, and/or undesirable debris. Hematopoietic components may also be displaced by hand, without any and/or without excess scraping or scrubbing to preserve the disinfected human placental tissue's membrane integrity and to further preserve various endogenous growth factors (e.g., IL-1ra, HGF, VEGFR1, HA, PDGF-BB, GAGs, and collagen) therein. As should be appreciated, the presence of blood, blood clots, blood components, and/or any other undesirable debris induces immunogenic responses. Therefore, removal of blood, blood clots, blood components, and/or any other undesirable debris is imperative to reduce immunogenicity and/or the probability of an immunogenic response, if any, of the end resulting sterilized human allograft when implanted/transplanted into a human subject in need thereof.

After step (b), the human placental tissue is subjected to at least one cleaning/wash step as depicted in step (c) of FIG. 1. During step (c), the human placental tissue is placed into an isotonic solution (and/or an iso-osmolar solution) to rinse away any extraneous non-human placental components and/or any other potential contaminants. In certain aspects, the isotonic solution comprises at least one of 1× phosphate buffered saline, isotonic saline, lactated ringers, Plasma-Lyte® (NaCl 5.26 g/L, KCl 0.37 g/L, Magnesium Chloride hexahydrate 0.30 g/L, Sodium Acetate trihydrate 3.68 g/L, Sodium Gluconate 5.02 g/L at pH 7.4), Normosol® (NaCl 5.26 g/L, KCl 0.37 g/L, Magnesium Chloride 0.30 g/L, Sodium Acetate anhydrous 2.22 g/L, Sodium Gluconate 5.02 g/L at pH 7.4), or any combination thereof. The washing step of step (c) may occur once and/or may be repeated one time, two times, three times, or four times with each wash step occurring for 5 to 15 minutes with a predetermined volume (e.g., 250 mL to 1000 mL, preferably 500 mL) of the isotonic solution at a temperature ranging from 4° C. to 20° C. Step (c) preferably occurs at low-temperature with the isotonic solutions having balanced pH, which further advantageously reduces and/or eliminates human placental tissue degradation and/or endogenous growth factor degradation (e.g., IL-1ra, HGF, VEGFR1, HA, PDGF-BB, GAGs, and collagen) during step (c). Although the above-mentioned isotonic solutions may be used, it should be further appreciated that no harsh chemicals/solutions such as harsh organic or harsh inorganic acids, harsh bases, and/or harsh peroxides (e.g., NaOH, carboxylic acids, HCl, $H_2O_2$) are used during step (c) or at any time during the method depicted in FIG. 1. In particular, the use of harsh organic or harsh inorganic acids, harsh bases, or harsh peroxides can detrimentally result in human placental tissue degradation as well as endogenous growth factor degradation and should be avoided for these reasons.

After step (c) and as further shown in FIG. 1, the human placental tissue is subjected to a dehydration/drying step (d). In particular, the human placental tissue is gently laid flat at ambient temperature for 2-12 hours in the biosafety cabinet with a circulating fan to dehydrate/dry the human placental tissue, or placed in a dehydrator for ½ hour to 6 hours, more preferably from 1 hours to 4 hours (at a temperature ranging 30° C. to 40° C.) to obtain the dehydrated human placental tissue. Slow dehydrating/drying of the human placental tissue advantageously preserves tissue structure, integrity, and the endogenous growth factors therein while advantageously avoiding damage frequently observed from freezing (e.g. freeze-drying) and/or drying at high temperatures (e.g. accelerated drying) human placental tissues. The end resulting dehydrated human placental tissue has a maximum water content ranging from 10 wt % to 15 wt %, which reduces the likelihood of any endogenous degradative processes reliant on the presence of water thereby further minimizing growth factor degradation during the method of FIG. 1.

After step (d), the dehydrated human placental tissue is resized during step (e) into dehydrated human placental tissue portions having predetermined sizes and predetermined shapes. When resizing the dehydrated human placental tissue into the dehydrated human placental tissue portions, a die having predetermined size(s) and/or dimension(s) and/or shape(s) may be used to precisely resize the dehydrated human placental tissue into dehydrated human placental tissue portions into the desired shape thereby ensuring for optimal tissue size, shape, and quality for each end resulting sterile human placental allografts produced by the methods disclosed herein. In certain aspects, the dehydrated human placental tissue portions is resized into a circular shape, a square shape, a rectangular shape, a rhomboid shape, an ovoid shape, a triangular shape, or any combination thereof. Each of these shapes may have various different sizes and/or dimensions for varied end uses and/or applications. In certain aspects, the predetermined sizes of the dehydrated placental tissue portions range from 1 cm×1 cm to 8 cm×8 cm for the rectangular and/or square shaped dehydrated placental tissue portions in which any endpoints within any of these ranges may serve as endpoints for any additional ranges falling therein. In certain aspects, the predetermined sizes of the dehydrated placental tissue portions range from, 8 mm diameter to 50 mm diameter for circular shaped dehydrated placental tissue portions in which any endpoints within any of these ranges may serve as endpoints for any additional ranges falling therein. In certain aspects, the dehydrated human placental tissue portions may further include a planar upper or lower surface, or the human placental tissue portion includes both planar upper and lower surfaces.

Figure 12A:
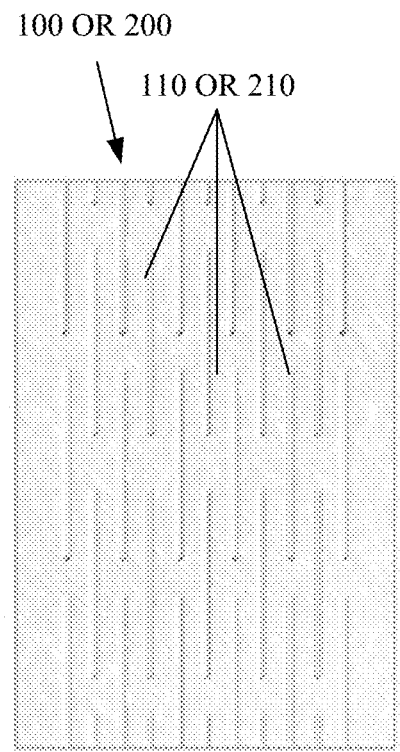
FIG. 12A depicts the sterile human placental allograft having a plurality of slits formed thereon in an unexpanded configuration.
Figure 12B:
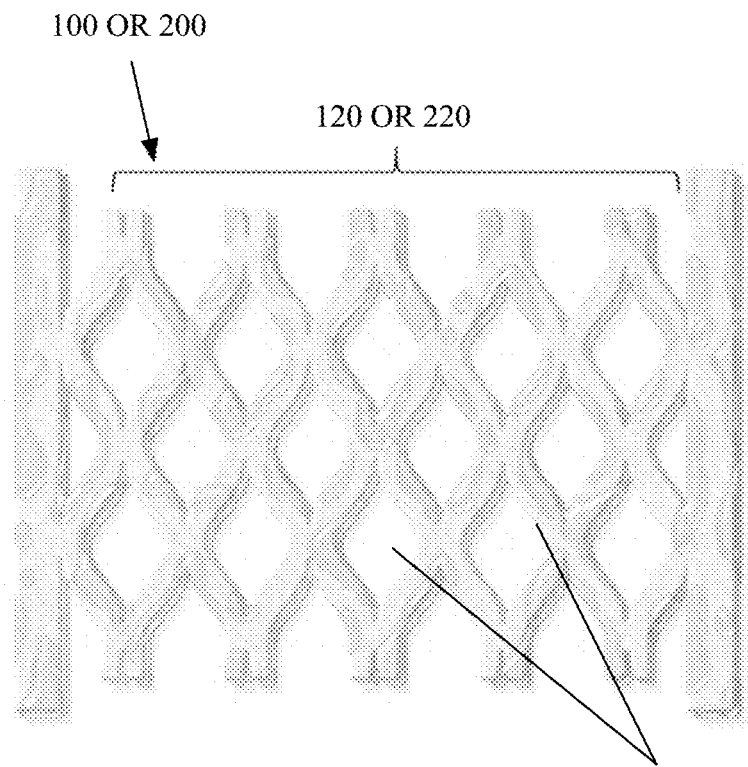
FIG. 12B depicts the human placental allograft of FIG. 12A in an expanded configuration having openings configured for wound exudate to flow from the wound and pass through the allograft in a direction from a lower surface of the allograft to the upper surface of the allograft.
Figure 13:
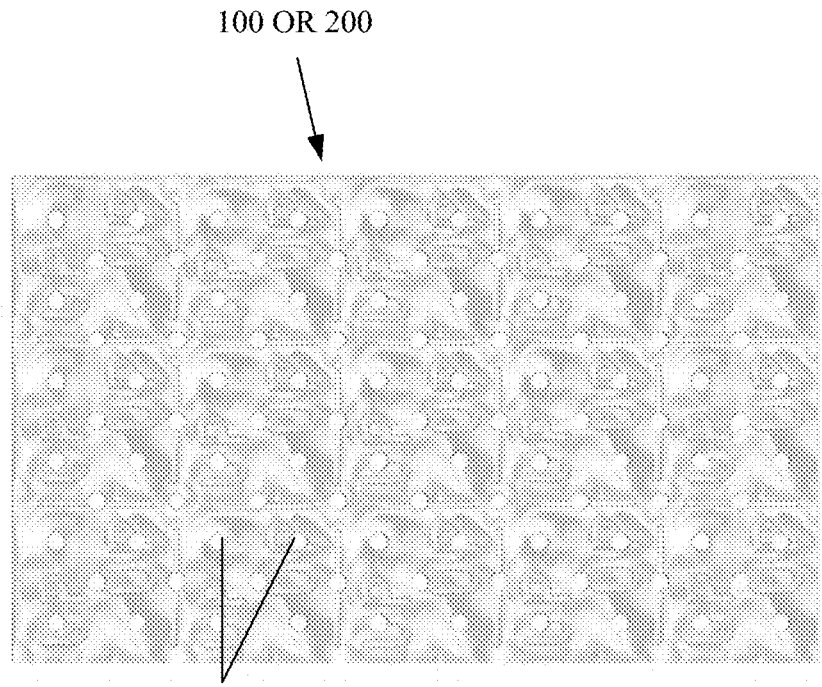
FIG. 13 depicts the sterile human placental allograft having a plurality of opening formed thereon such that the lower and upper surfaces of the allograft are in fluid communication with one another and the openings are configured for wound exudate to flow from the wound and pass through allograft in a direction from a lower surface of the allograft to the upper surface of the allograft.

After step (e), the dehydrated human placental tissue portions of step (e) (resized portions having the desired predetermined shape(s) and size(s)) are subsequently sterilized during step (f) thereby forming the sterile human placental allograft. Moreover and as shown in FIGS. 1 and 12A-14D, in certain aspects before step (f) (i.e., after step (d) and after step (e) or after step (d) and before step (e)), slits, openings, and/or fenestrations are formed on (and through) the human placental allograft and/or in the dehydrated human placental portions of such that the sterile human placental allograft (resulting after step (f)) includes a plurality of slits, openings, or fenestrations (e.g., flaps) formed on an upper surface of the allograft and having corresponding slits (e.g., aligned and/or axially aligned), openings or fenestrations (flaps) formed on a lower surface of the allograft such that the slits, openings, or fenestrations (e.g., flaps) formed on the upper surface of the allograft are in fluid communication with the corresponding slits, openings, or fenestration (e.g., flaps) formed on the lower surface of the allograft such that, when in use, the allografts allow wound exudate to flow from a wound and pass through the allograft in a direction from a lower surface of the allograft to the upper surface of the allograft thereby facilitating wound drainage, wound healing, or a combination thereof. In view of the above, FIG. 12A depicts a top view of the sterile human placental allograft disclosed herein having a plurality of slits (110 or 210) formed thereon in an unexpanded configuration and FIG. 12B depicts a top view of the human placental allograft of FIG. 12A in an expanded configuration (120 or 220) having openings (110 or 210 formed from the slits when the allograft is expanded) arranged in a predetermined pattern (e.g., a tessellated pattern and/or a tessellated pattern having rhomboid or semi-rhomboid shaped openings) that are configured for wound exudate to flow from the wound and pass through the allograft in a direction from a lower surface of the allograft to the upper surface of the allograft. FIG. 13 depicts a top view of the sterile human placental allograft (100 or 200) having a plurality of openings (130 or 230) formed thereon such that the lower and upper surfaces of the allograft are in fluid communication with one another and the openings are configured for wound exudate to flow from the wound and pass through allograft in a direction from a lower surface of the allograft to the upper surface of the allograft. In certain aspects, the slits and/or openings may be formed on the allograft using conventional devices such as dies or cutting devices.

Figure 14A:
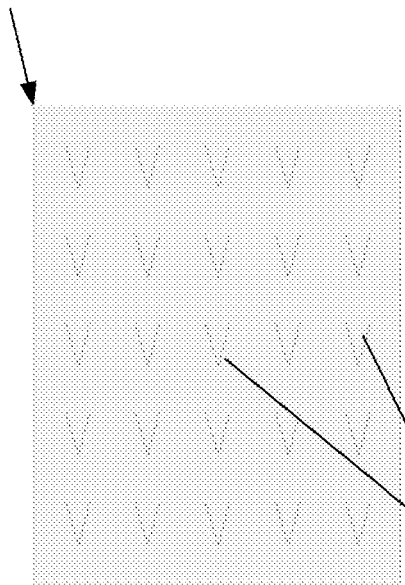
FIG. 14A, FIG. 14B, and FIG. 14C each depict the sterile human placental allograft having a plurality of fenestrations (a plurality of flaps having predetermined shapes) formed thereon such that the fenestrations are configured for wound exudate to flow from the wound and pass through allograft in a direction from a lower surface of the allograft to the upper surface of the allograft
Figure 14B:
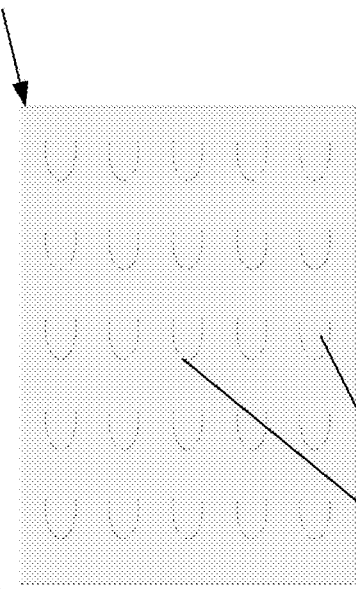
Figure 14C:
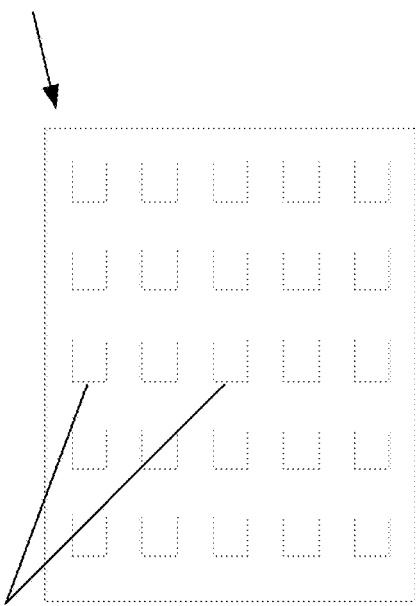
Figure 14D:
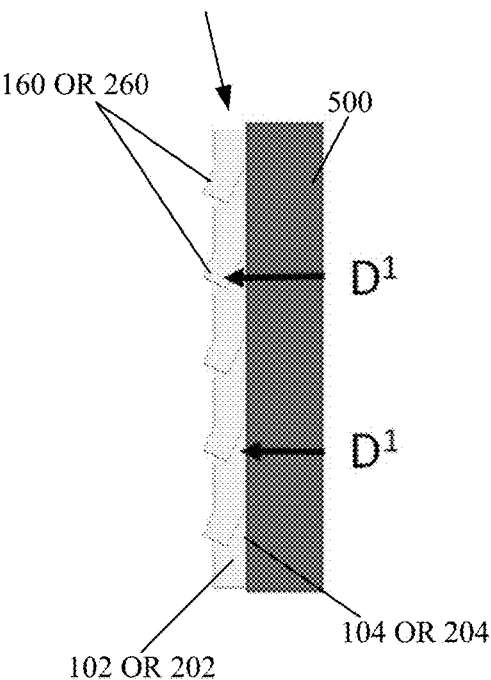
FIG. 14D is a side view of the fenestrations shown in FIG. 14C.

In certain aspects and as shown in FIGS. 14A-14D, 16A and 16B, the human sterile placental allograft (100 or 200) includes a plurality of fenestrations (140 or 240, 150 or 250, 160 or 260) formed on the sterile human placental allograft that are configured for flow of wound exudate from a wound through the sterile human placental allograft (100 or 200) in a direction from the lower surface of the sterile human placental allograft to the upper surface of the sterile human placental allograft to facilitate wound drainage, wound healing, or a combination thereof. In this aspect and as shown in FIGS. 14C and 14D, each fenestration is a flap configured to open when wound exudate and/or other bodily fluids are flowing through the sterile human placental allograft and to close when no wound exudate and/or other bodily fluids are flowing through the sterile human placental allograft. Each flap is sufficiently spaced apart relative to one another to allow for wound exudate to flow therefrom without interfering with the opening and closing of any adjacent flaps.

Figure 15:
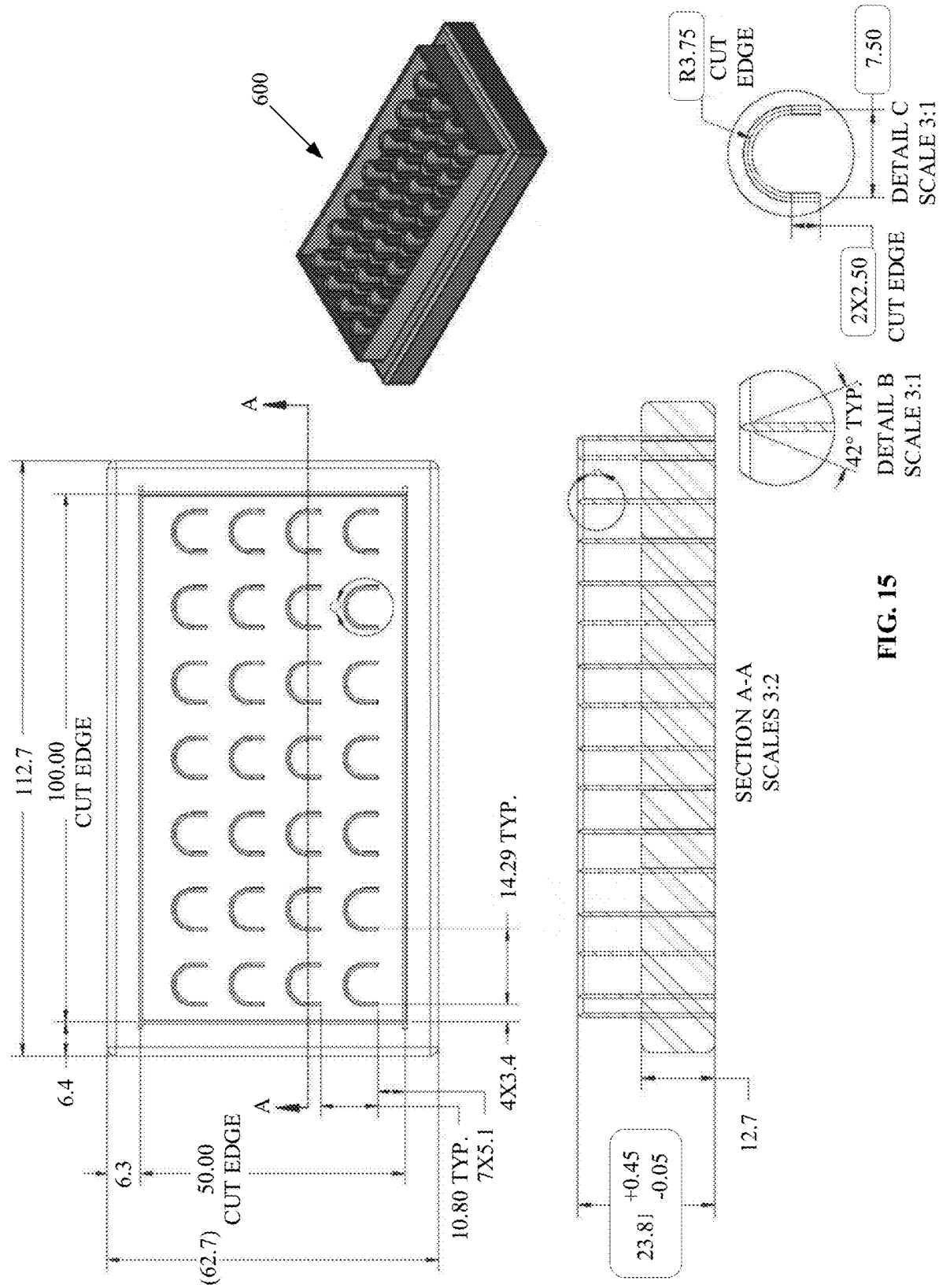
FIG. 15 depicts die cutting devices that form the plurality of fenestrations in the allografts shown in FIGS. 14A-14C respectively.
Figure 16A:
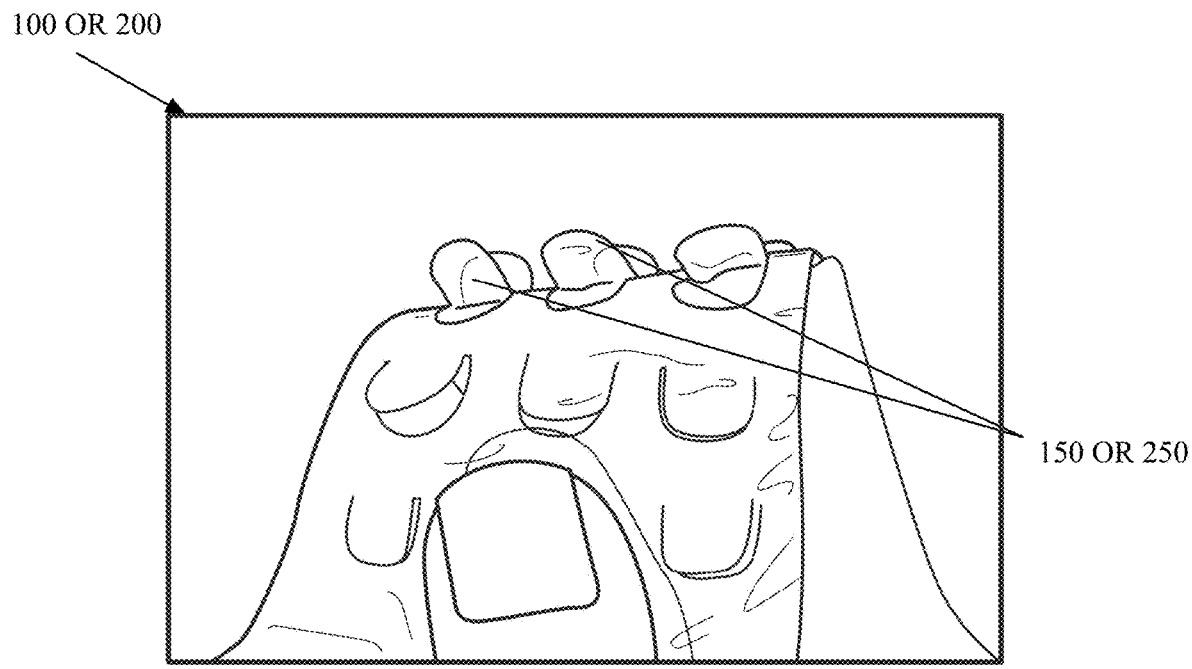
FIG. 16A is a photograph of the sterile human placental allograft having a plurality of fenestrations formed thereon.
Figure 16B:
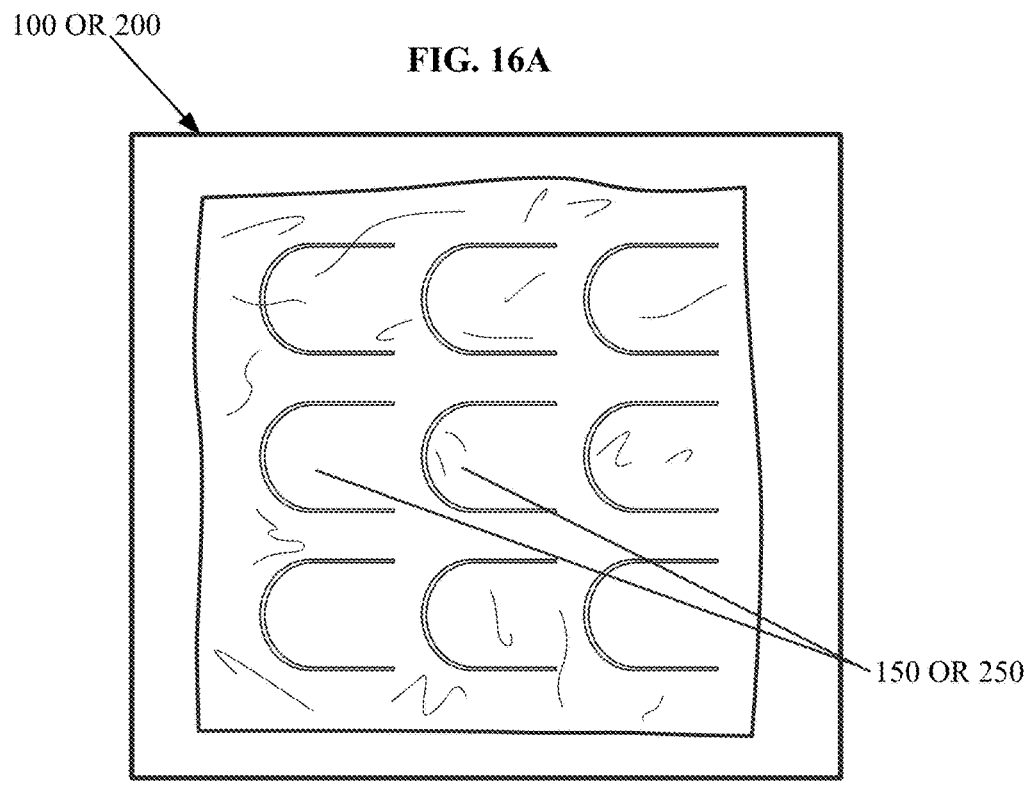
FIG. 16B is another photograph of the sterile human placental allograft having a plurality of fenestrations formed thereon.

FIGS. 14A-14C depict allografts having fenestrations formed thereon that are closed and/or in a closed configuration. FIG. 14D is schematic depiction of a cross-section and/or a side view of the allograft (100 or 200), when in use and positioned on a wound (500), showing open flaps (160 or 260) moved in a direction ($D^1$) by wound exudate and/or other bodily fluids originating from the wound (500) and flowing away from the wound (500), the lower surface (104 or 204), and the upper surface (102 or 202) of the sterile human placental allograft thereby facilitating wound drainage, wound healing, or a combination thereof. In certain aspects and as further shown in FIGS. 14A-14D, the fenestrations have predetermined shapes, which include a "V" shape (140 or 240), a "U" shape (150 or 250), a semi-"U" shape (160 or 260), a semi-square shape, a semi-rectangular shape, or combinations thereof. Moreover, FIG. 16A is a photograph of the sterile human placental allograft having a plurality of fenestrations formed thereon, and FIG. 16B is another photograph of the sterile human placental allograft having a plurality of fenestrations formed thereon. The above discussed fenestrations (e.g., flaps) are formed by flat pressing or roll pressing the allograft (preferably pre-sterilization (e.g., E-beam sterilization)) on a die (600) or cutting apparatus, as shown for example in FIG. 15, having predetermined shapes formed thereon to cut and form fenestrations in the allograft, with the fenestrations having a predetermined shape (e.g., V-shaped, U-shaped or semi-U-shaped notches).

In certain aspects, the sterilizing step (f) includes sterilizing the dehydrate human placental tissue portions with e-beam irradiation to a sterility assurance level (SAL) of $10^{-6}$, as determined by dose mapping by E-beam vendor, thereby forming the sterile human placental allograft in which the SAL, expressed as $10^{-N}$, is the expected probability of surviving organisms post treatment (e.g., expected probability of any surviving microorganism after sterilization is $10^{-6}$ or less). Before sterilization, the dehydrated human placental tissue portions of step (e) (resized portions having the desired predetermined shape(s) and size(s)) may be first placed into either into primary and/or secondary packaging and then subjected to low-dose E-beam irradiation to produce the sterile human placental allograft, which is ready for end use (after removal from the primary or secondary packaging). Alternatively, the dehydrated human placental tissue portions of step (e) (resized portions having the desired predetermined shape(s) and size(s)) may be first subjected to low-dose E-beam irradiation to produce the sterile human placental allograft and then may be subsequently placed into sterile packaging while maintaining sterility of the sterile human placental allograft for subsequent end use.

Low-dose E-beam irradiation is particularly preferred to other sterilization methods because these other methods require direct access to the human placental tissue and leave residual contaminants (e.g. ethylene oxide) on the end resulting allograft, which may result in an immunogenic response when the resulting allograft is used, or require exposure of the tissue to extended periods of higher dose irradiation (e.g. gamma irradiation), which unnecessarily degrades structural integrity and endogenous growth factors of the placental tissue.

Figure 10A:
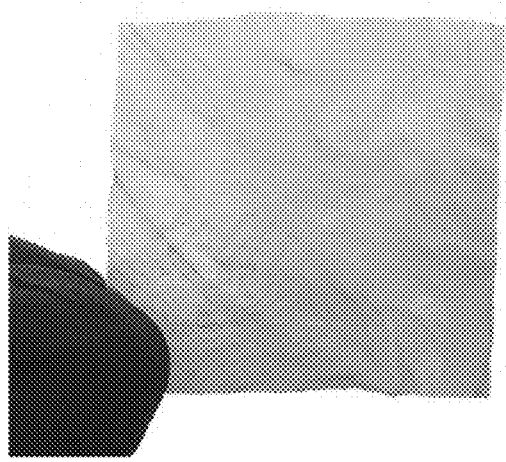
FIG. 10A is a photograph of the sterile human placental allograft of FIG. 8A (i.e., Example 1)
Figure 11A:
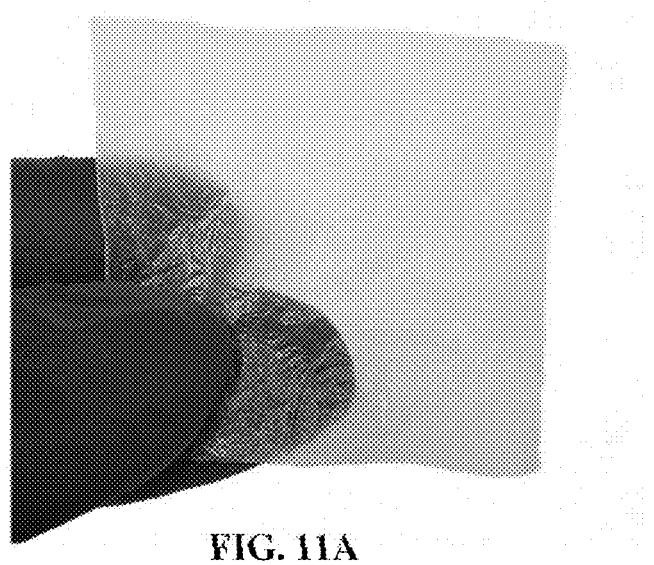
FIG. 11A is a photograph of the sterile human placental allograft of FIG. 9 (i.e., Example 2), and FIG. 11B a photograph of the commercially available product of FIG. 9 (i.e., Comp Ex. 3)
Figure 11B:
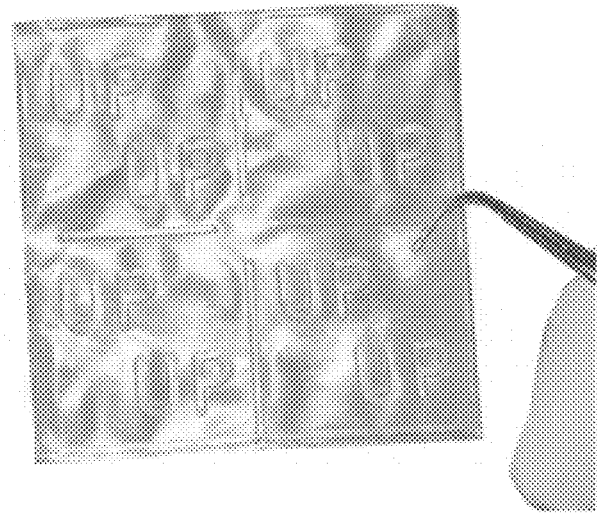

As further shown in FIGS. 10A and 11A, the sterile human placental allografts produced by the above methods have predetermined shapes and sizes. As alluded to above, the sterile human placental allografts may be circular shaped, square shaped, rectangular shaped, rhomboid shaped, ovoid shaped, triangular shaped, or any combination thereof. Each of these shapes may have various different sizes and/or dimensions for varied end uses and/or applications. In certain aspects, the predetermined sizes of the sterile human placental allografts range from 1 cm×1 cm to 8 cm×8 cm for rectangular and/or square shaped sterile human placental allografts in which any endpoints within any of these ranges may serve as endpoints for any additional ranges falling therein and ranging from 2 mm diameter to 50 mm diameter for circular and/or round sterile human placental allografts in which any endpoints within any of these ranges may serve as endpoints for any additional ranges falling therein. In certain aspects, the sterile human placental allografts may further include a planar upper or lower surface, or the sterile human placental allografts includes both planar upper and lower surfaces. Moreover, and as shown in FIGS. 10A and 11A, the sterile human placental allografts may have a thickness ranging from 0.01 mm to 0.2 mm, and may further have a translucent appearance.

Upon concluding step (f), all sterile human placental allografts are subjected to quality control(s) and lot control(s). All records from the human placental tissue processing from the above-mentioned methods are finally reviewed by Medical Director(s) and Site Quality Head to ensure a thorough quality assurance review and compliance of the resulting sterile human allografts with the applicable government rules, compliance, and procedures.

Sterilized Human Placental Allograft

The sterile human placental allografts disclosed herein can be produced by the methods disclosed herein. The allografts disclosed herein are safe, biocompatible, growth factor-rich sterile human placental allografts having much higher amounts of growth factors therein than conventional allografts in the field that better mimic the growth factor profile of human placenta in vivo than other conventional allografts, thereby achieving better therapeutic outcomes for dental applications and wound healing and/or better cosmetic/aesthetic outcomes depending on the application. The sterile human placental allografts disclosed herein are preferably non-immunogenic—resulting in little or no immune response post-implantation/transplantation into a human recipient and/or post-application to a wound in and/or on the subject in need thereof.

Figure 6:
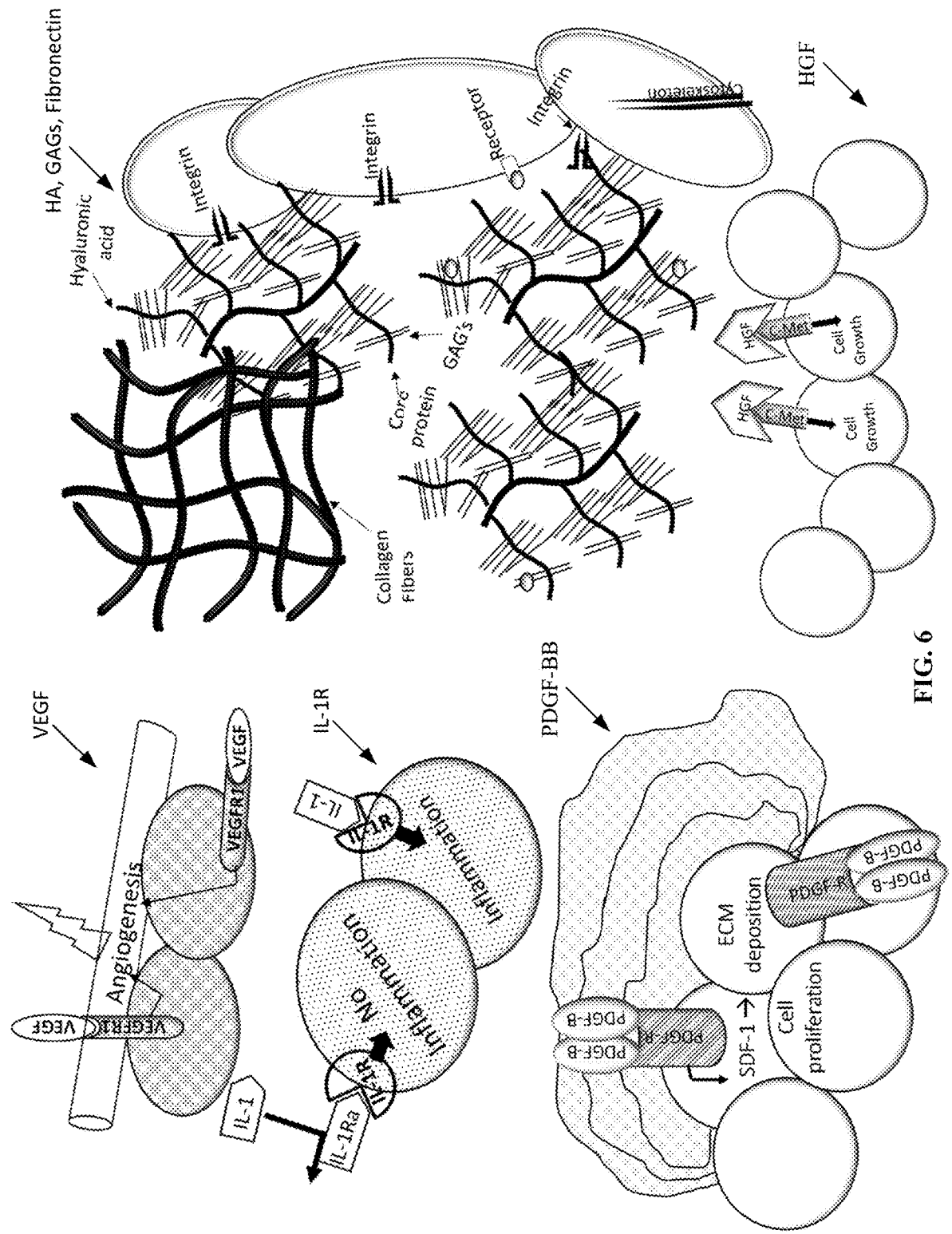
FIG. 6 depicts various human endogenous pathways activated by vascular endothelial growth factor receptor 1 (VEGFR1), interleukin-1 receptor antagonist (IL 1ra), hepatocyte growth factor (HGF), hyaluronic acid (HA), glycosaminoglycans (GAGs) and platelet derived growth factor subunit B homodimer (PDGF-BB) are associated with cellular remodeling, wound healing, and other human endogenous pathways in vivo.
Figure 7:
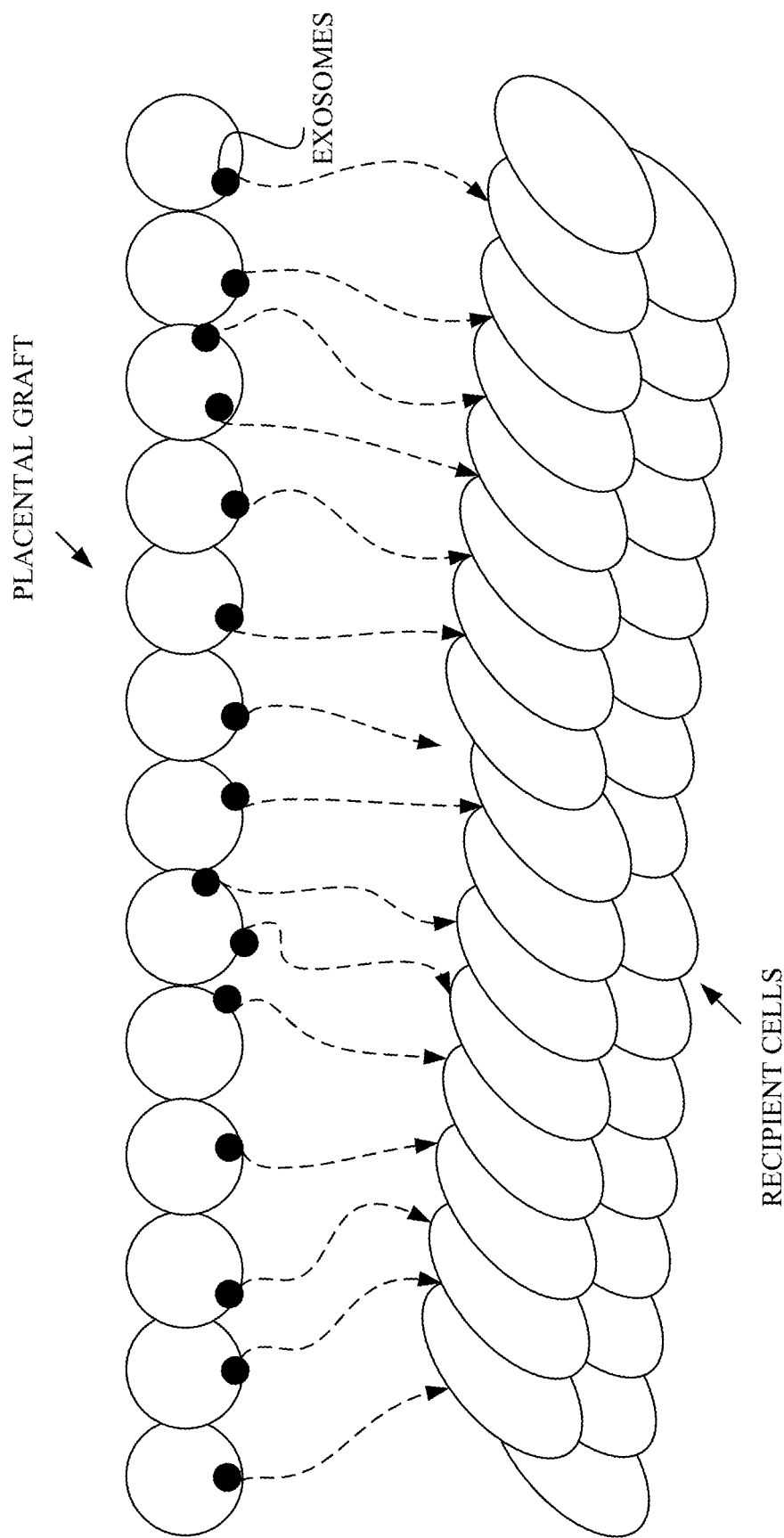
FIG. 7 depicts the retention of available exosomes in the sterile human allografts prepared from the methods disclosed herein.

The sterile human placental allografts disclosed herein are particularly rich in interleukin-1 receptor antagonist (IL-1ra), hepatocyte growth factor (HGF), vascular endothelial growth factor receptor 1 (VEGFR1), hyaluronic acid (HA), platelet derived growth factor subunit B homodimer (PDGF-BB), glycosaminoglycans (GAGs); and collagen when compared with conventional allografts. Moreover, FIG. 6 schematically depicts various human endogenous pathways activated by vascular endothelial growth factor receptor 1 (VEGFR1), interleukin-1 receptor antagonist (IL-1ra), hepatocyte growth factor (HGF), hyaluronic acid (HA), glycosaminoglycans (GAGs) and that), platelet derived growth factor subunit B homodimer (PDGF-BB) are associated with cellular remodeling, wound healing, and other human endogenous pathways in vivo. In particular, IL-1ra binds non-productively to the IL-1 (pro-inflammatory cytokine) receptor, preventing IL-1 (inflammatory molecule) from sending a signal. This results in modulation of a variety of IL-1 related immune and inflammatory responses. HGF is cellular growth, motility and morphogenic factor secreted by mesenchymal cells. It has been shown to have a major role in embryonic organ development, specifically in myogenesis, in adult organ regeneration, and in wound healing. Importantly, increased expression of HGF has been associated with the enhanced and scarless wound healing capabilities of fibroblast cells isolated from the oral mucosa tissue. VEGFR1 acts as a cell-surface receptor for VEGF-A, VEGF-B and PGF for the development of embryonic vasculature, the regulation of angiogenesis, cell survival and cell migration. VEGFR1 can promote endothelial cell proliferation, survival and angiogenesis in adulthood. Its function in promoting cell proliferation seems to be cell-type specific. For example, it promotes PGF-mediated proliferation of endothelial cells, but does not promote proliferation of normal fibroblasts (in vitro). PDGF-BB is a powerful promoter of cell proliferation and plays a significant role in angiogenesis (blood vessel formation), including the growth of blood vessels from already-existing blood vessel tissue. PDGF-BB promotes the proliferation and directed migration of mesenchymal cells and significantly augments the influx of inflammatory cells, accelerating extracellular matrix and collagen formation and thus reducing overall wound healing time. Glycosaminoglycans (GAGs) are present in all mammalian tissues where they interact with other ECM components to organize and form structural scaffolding suitable for remodeling. GAGs also modulate cell growth and proliferation, cell adhesion, anticoagulation, and wound repair. Hyaluronic acid (HA) is a well-documented chief component of the extracellular matrix. HA is a non-sulfated glycosaminoglycan that, among other things, provides a backbone for sulfated glycosaminoglycans. HA also binds integrins resulting in stabilized ECM and absorbs water which is another chief component of the ECM. The high molecular mass of HA results in unique biophysical properties, such as, high viscoelasticity and high colloid osmotic pressure. Additionally, HA leads to extracellular matrix stabilization, water maintenance and regulation of protein distribution. Collagen is the most abundant protein in the body and a key component of the extracellular matrix, and during wound healing, collagen attract fibroblasts and encourage deposition of new collagen as well as bind and inactivate excessive matrix metalloproteinase (degradation). Exosomes are vesicles ranging from 30 to 200 nm that enable intercellular communication without direct cell-cell contact. They are released through the membrane of cells [Keller 2006, Zomer 2010](in this case, placental cells) and taken up by the tissues where they release signals that came from the placental tissue. As a result, signals for development and regeneration are delivered to cells of the damaged tissue. Exosomes are enriched in small RNA species including miRNAs, which have been demonstrated to be functional in the recipient cells [Montecalvo 2008]. Exosomes have gained momentum as a safe and effective therapy for skin wounds/disorders [Subhan 2021].

In certain aspects and as further shown in FIGS. 3A-3F, FIGS. 5A and 5B, and FIG. 10A (100), the sterile human placental allograft is intact in cross-section in which the human amnion layer and the human chorion layer have an intact human intermediate spongy layer positioned there between connecting the human amnion layer to the human chorion layer, wherein these allografts include at least one, at least two, at least three, at least four, at least five, at least six, at least seven, or at least eight of the following: (a) interleukin-1 receptor antagonist (IL-1ra) ranging from 200 to 7800 pg/cm$^2$ and more preferably ranging from 1000 to 6000 pg/cm$^2$ (b) hepatocyte growth factor (HGF) ranging from 500 to 8500 pg/cm$^2$ and more preferably ranging from 1000 to 7500 pg/cm$^2$; (c) vascular endothelial growth factor receptor 1 (VEGFR1) ranging from 1000 to 2750 pg/cm$^2$ and more preferably ranging from 900 to 2500 pg/cm$^2$; (d) hyaluronic acid (HA) ranging from $5.0\times10^6$ to $1.5\times10^8$ pg/cm$^2$ and more preferably ranging from $1.5\times10^7$ to $1.0\times10^8$ pg/cm$^2$; (e) platelet derived growth factor subunit B homodimer (PDGF-BB) ranging from 150 to 400 pg/cm$^2$ and more preferably ranging from 200 to 375 pg/cm$^2$; (f) glycosaminoglycans (GAGs); (g) collagen, and (h) exosomes in which any endpoints within any of the above-mentioned ranges may serve as endpoints for any additional ranges falling therein. The above referenced concentrations were obtained/calculated by the "standardization" calculations and methods disclosed herein. It should be further appreciated that these allografts are configured for specific dental, wound healing, and cosmetic purposes are preferably implantable/transplantable in a subject in need thereof or may be applied to superficial wounds (e.g., diabetic ulcers). In this aspect, these sterile human placental allografts have predetermined shapes and sizes in which the predetermined shapes may include, but are not limited to, circular shaped, square shaped, rectangular shaped, rhomboid shaped, ovoid shaped, triangular shaped, or any combination thereof. Moreover, the predetermined sizes of the sterile human placental allografts include dimensions ranging from 1 cm×1 cm to 8 cm×8 cm in which any endpoints within any of these ranges may serve as endpoints for any additional ranges falling therein and/or diameters ranging from 8 mm diameter to 50 mm diameter in which any endpoints within any of these ranges may serve as endpoints for any additional ranges falling therein. Depending on the specific use, these sterile human placental allografts may further include a planar upper or lower surface, or these sterile human placental allografts includes both planar upper and lower surfaces. Further depending on the specific use, the sterile human placental allografts may have a thickness ranging from 0.08 mm to 0.2 mm, and may further have a translucent appearance as shown, for example, in FIG. 10A.

In certain aspects and as further shown in FIGS. 2A-2F, FIGS. 4A and 4B, and FIG. 11A (200), the sterile human placental allograft consists essentially of the human amnion membrane, and/or in further aspects, the sterile human placental allograft consists of the human amnion membrane. In each of these aspects, the sterile human placental allograft (consisting essentially of and/or consisting of the amnion membrane) include at least one, at least two, at least three, at least four, at least five, at least six, at least seven, or at least eight of the following: (a) interleukin-1 receptor antagonist (IL-1ra) ranging from 150 to 1800 pg/cm$^2$ and more preferably ranging from 200 to 1500 pg/cm$^2$ (b) hepatocyte growth factor (HGF) ranging from 75 to 400 pg/cm$^2$ and more preferably ranging from 150 to 350 pg/cm$^2$; (c) vascular endothelial growth factor receptor 1 (VEGFR1) ranging from 50 to 250 pg/cm$^2$ and more preferably ranging from 75 to 200 pg/cm$^2$; (d) hyaluronic acid (HA) ranging from $1.1\times10^6$ to $2.0\times10^7$ pg/cm$^2$ and more preferably ranging from $1.5\times10^6$ to $1.8\times10^7$ pg/cm$^2$; (e) platelet derived growth factor subunit B homodimer (PDGF-BB) ranging from 200 to 500 pg/cm$^2$ and more preferably ranging from 250 to 450 pg/cm$^2$; (f) glycosaminoglycans (GAGs); (g) collagen, and (h) exosomes in which any endpoints within any of the above-mentioned ranges may serve as endpoints for any additional ranges falling therein. The above referenced concentrations were obtained by the "standardization" calculations and methods disclosed herein. It should be further appreciated that these allografts are configured for specific dental, wound healing, and cosmetic purposes are preferably implantable/transplantable in a subject in need thereof or may be applied to superficial wounds (e.g., diabetic ulcers). In this aspect, these sterile human placental allografts have predetermined shapes and sizes in which the predetermined shapes may include, but are not limited to, circular shaped, square shaped, rectangular shaped, rhomboid shaped, ovoid shaped, triangular shaped, or any combination thereof. Moreover, the predetermined sizes of the sterile human placental allografts include dimensions ranging from 1 cm×1 cm to 8 cm×8 cm in which any endpoints within any of these ranges may serve as endpoints for any additional ranges falling therein and/or diameters ranging from 8 mm diameter to 50 mm diameter in which any endpoints within any of these ranges may serve as endpoints for any additional ranges falling therein. Depending on the specific use, these sterile human placental allografts may further include a planar upper or lower surface, or these sterile human placental allografts includes both planar upper and lower surfaces. Further depending on the specific use, the sterile human placental allografts may have a thickness ranging from 0.01 mm to 0.05 mm, and may further have a translucent appearance as shown in, for example, FIG. 11A.

Moreover and as shown in FIGS. 1 and 12A-14D, in certain aspects the allografts disclosed herein may include slits, openings, and/or fenestrations are formed on (and through) the human placental allograft such that the sterile human placental allograft includes a plurality of slits, openings, or fenestrations (e.g., flaps) formed on an upper surface of the allograft and has corresponding slits (e.g., aligned and/or axially aligned), openings or fenestrations (flaps) formed on a lower surface of the allograft such that the slits, openings, or fenestrations (e.g., flaps) formed on the upper surface of the allograft are in fluid communication with the corresponding slits, openings, or fenestration (e.g., flaps) formed on the lower surface of the allograft such that, when in use, the allografts allow wound exudate to flow from a wound and pass through the allograft in a direction from a lower surface of the allograft to the upper surface of the allograft thereby facilitating wound drainage, wound healing, or a combination thereof. In view of the above, FIG. 12A depicts a top view of the sterile human placental allograft disclosed herein having a plurality of slits (110 or 210) formed thereon in an unexpanded configuration and FIG. 12B depicts a top view of the human placental allograft of FIG. 12A in an expanded configuration (120 or 220) having openings (110 or 210 formed from the slits when the allograft is expanded) arranged in a predetermined pattern (e.g., a tessellated pattern and/or a tessellated pattern having rhomboid or semi-rhomboid shaped openings) that are configured for wound exudate to flow from the wound and pass through the allograft in a direction from a lower surface of the allograft to the upper surface of the allograft. FIG. 13 depicts a top view of the sterile human placental allograft (100 or 200) having a plurality of openings (130 or 230) formed thereon such that the lower and upper surfaces of the allograft are in fluid communication with one another and the openings are configured for wound exudate to flow from the wound and pass through allograft in a direction from a lower surface of the allograft to the upper surface of the allograft. In certain aspects, the slits and/or openings may be formed on the allograft using conventional devices such as dies or cutting devices.

In certain aspects and as shown in FIGS. 14A-14D, 16A and 16B, the human sterile placental allograft (100 or 200) includes a plurality of fenestrations (140 or 240, 150 or 250, 160 or 260) formed on the sterile human placental allograft that are configured for flow of wound exudate from a wound through the sterile human placental allograft (100 or 200) in a direction from the lower surface of the sterile human placental allograft to the upper surface of the sterile human placental allograft to facilitate wound drainage, wound healing, or a combination thereof. In this aspect and as shown in FIGS. 14C and 14D, each fenestration is a flap that is configured to open when wound exudate and/or other bodily fluids are flowing through the sterile human placental allograft and to close when no wound exudate and/or other bodily fluids are flowing through the sterile human placental allograft. Each flap is sufficiently spaced relative to one another to allow for wound exudate flow therefrom without interfering with the opening and closing of any adjacent flaps. For example, the fenestrations (e.g., flaps) are spaced about 14 mm apart from the center of one fenestration (flap) to the center of another fenestration (flap). Depending on the overall size of the allograft fenestration (flap) spacing may be varied. For example, a 5×10 cm allograft may have 28 notches wherein each fenestration (flap) is spaced apart from another fenestration (flap) approximately 14 mm (spacing as described immediately above) apart and with each fenestration (flap) being approximately 7.5 mm wide. The fenestrations (flaps) advantageously allow the fluids within a wound bed to exit the space, carries this risk of surface area loss and interruption of matrix. Fenestrations (flaps) address these issues because the allograft does not lose integrity and/or the matrix is not interrupted, which can allow exit of fluids from the wound without loss of surface area. Furthermore, the allografts with fenestrations (flaps) as disclosed herein advantageously retain the direction and organization of the matrix, hence promotes ECM deposition and stabilization while providing factors that play crucial roles in ECM composition and wound healing.

FIGS. 14A-14C depict allografts having fenestrations formed thereon that are closed and/or in a closed configuration. FIG. 14D is schematic depiction of a cross-section and/or a side view of the allograft (100 or 200), when in use, showing open flaps (160 or 260) moved in a direction ($D^1$) by wound exudate and/or other bodily fluids originating from the wound flowing away from the wound (500), the lower surface (104 or 204), and the upper surface (102 or 202) of the sterile human placental allograft thereby facilitating wound drainage, wound healing, or a combination thereof. In certain aspects and as further shown in FIGS. 14A-14D, the fenestrations have predetermined shapes, which include a "V" shape (140 or 240), a "U" shape (150 or 250), a semi-"U" shape (160 or 260), or combinations thereof. Moreover, FIG. 16A is a photograph of the sterile human placental allograft having a plurality of fenestrations formed thereon, and FIG. 16B is another photograph of the sterile human placental allograft having a plurality of fenestrations formed thereon. The above discussed fenestrations (e.g., flaps) are formed by flat pressing or roll pressing the allograft (preferably pre-sterilization (e.g., E-beam sterilization)) on a die (600), as shown for example in FIG. 15, having predetermined shapes formed thereon to cut and form fenestrations in the allograft, with the fenestrations having a predetermined shape (e.g., V-shaped, U-shaped or semi-U-shaped notches).

Kits And Methods of Use

Also disclosed herein are kits comprising the sterile human placental allografts disclosed herein packaged in a sterile container. Upon opening the sterile container, the sterile human placental allograft packaged therein is ready for the desired end use. The sterile human allografts are configured for specific dental, wound healing, and/or cosmetic purposes and are preferably implantable/transplantable in a subject in need thereof or may be applied to superficial wounds (e.g., diabetic ulcers). As alluded to above, the sterile human placental allografts disclosed herein are preferably non-immunogenic—resulting in little or no immune response post-implantation/transplantation into and/or topical application to a human recipient.

In certain aspects, further disclosed are methods of treating wounds in a human subject in need thereof comprising contacting the wound with a sterile human placental allograft for a predetermined time period to facilitate wound healing in the human subject in need thereof. The predetermined time period includes from 3 days to 30 days for implantation uses and from 1 day to 5 days for topical uses. In certain aspects, the sterile human placental allograft is implanted in the subject in need thereof in which the wound is an internal wound within the subject in need thereof and/or a dental wound, thereby facilitating wound healing by elution/diffusion of the growth factors from the sterile human placental allograft into the wound. Moreover, the sterile humane placental allograft remains in the subject in need thereof acting as a scaffold for cellular and tissue remodeling post-elution/diffusion of the growth factors from the sterile human placental allograft into the wound, and the allograft eventually is resorbed within the subject in need thereof. In certain other aspects, the sterile human placental allograft is topically applied to the wound in the human subject in need thereof. Topical applications of the sterile human placental allograft may be used to treat, for example, diabetic ulcers (e.g., diabetic foot ulcers) and/or other regular-shaped or irregular shaped topical wounds (to the epidermis, dermis, and/or hypodermis) in a human subject in need thereof. The sterile human placental allograft is placed topically on a wound in a subject in need thereof for a predetermined period of time, thereby facilitating wound healing by elution/diffusion of the growth factors from the sterile human placental allograft onto and into the wound.

In an embodiment, the method further comprises either before step (a) or during step (a) disinfecting the human placental tissue with at least one of a bactericidal composition, a tuberculocidal composition, a fungicidal composition, a virucidal composition, or any combination thereof, wherein the at least one of a bactericidal composition, tuberculocidal composition, fungicidal composition, virucidal composition, or any combination thereof includes an isopropyl alcohol at a concentration of 70% to 100%; and/or wherein each wash step (c) is at a temperature ranging from 4 to 15° C. for a time-period of from 5 minutes to 15 minutes; and/or wherein the dehydrating step (d) is at a temperature ranging from 20 to 40° C. for a time-period of from 60 minutes to 4.5 hours; and/or wherein the sterilizing step (f) comprises sterilizing with e-beam irradiation.

In an aspect, the present invention relates to a method of preparing a sterile human placental allograft comprising:
(a) providing a human placental tissue from a donor within 24 hours to 72 hours post-childbirth, wherein either before step (a) or during step (a) disinfecting the human placental tissue with at least one of a bactericidal composition, a tuberculocidal composition, a fungicidal composition, a virucidal composition, or any combination thereof, wherein the at least one of a bactericidal composition, tuberculocidal composition, fungicidal composition, virucidal composition, or any combination thereof includes an isopropyl alcohol at a concentration of 70% to 100%;
(b) removing any visible blood, blood clots, and/or blood components from the human placental tissue without scraping or scrubbing the human placental tissue to preserve structural integrity of the human placental tissue;
(c) washing the human placental tissue in an isotonic solution while maintaining the structural integrity of the human placental tissue at a temperature ranging from 4 to 15° C. for a time-period of from 5 minutes to 15 minutes;
(d) dehydrating the human placental tissue thereby forming the dehydrated human placental tissue at a temperature ranging from 20 to 40° C. for a time-period of from 60 minutes to 4.5 hours;
(e) resizing the dehydrated human placental tissue into dehydrated human placental tissue portions having predetermined sizes; and
(f) sterilizing the dehydrated human placental tissue portions of step (e) with e-beam irradiation thereby forming the sterile human placental allograft.

In an aspect, the present invention relates to a sterile human placental allograft (preferably according to the present invention) for use in the treatment of a wound.

In an aspect, the present invention relates to a sterile human placental allograft (preferably according to the present invention) for use in the treatment of a wound in a human subject in need thereof, the treatment comprising contacting the wound with said sterile human placental allograft for a predetermined time period to facilitate wound healing in the human subject in need thereof.

The sterile human placental allograft for use, wherein the sterile human placental allograft is implanted in the subject in need thereof. The sterile human placental allograft for use, wherein the wound is an internal wound within the subject in need thereof and/or a dental wound. The sterile human placental allograft for use, wherein the sterile human placental allograft is topically applied to the wound in the human subject in need thereof. The sterile human placental allograft for use, wherein the wound is a diabetic ulcer. The sterile human placental allograft for use, wherein the wound is a diabetic foot ulcer.

Working Examples

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature if not listed, and pressure is at or near atmospheric. There are numerous variations and combinations of conditions, e.g., component concentrations, temperatures, pressures and other reaction ranges and conditions that can be used to optimize the product purity and yield obtained from the described process. Only reasonable and routine experimentation will be required to optimize such process conditions.

FIGS. 8A-11B provide graphs and photographs of the exemplary sterile human allografts (Example 1 and Example 2) prepared by the methods/processes disclosed herein and further compared to various commercially available sterile human allografts (Comparative Examples 1, 2, and 3). These graphs and photographs further evidence visual distinctions between the exemplary sterile human allografts disclosed herein as well as the drastically differing growth factor profiles when compared with the various commercially available sterile human allografts.

Figure 8A:
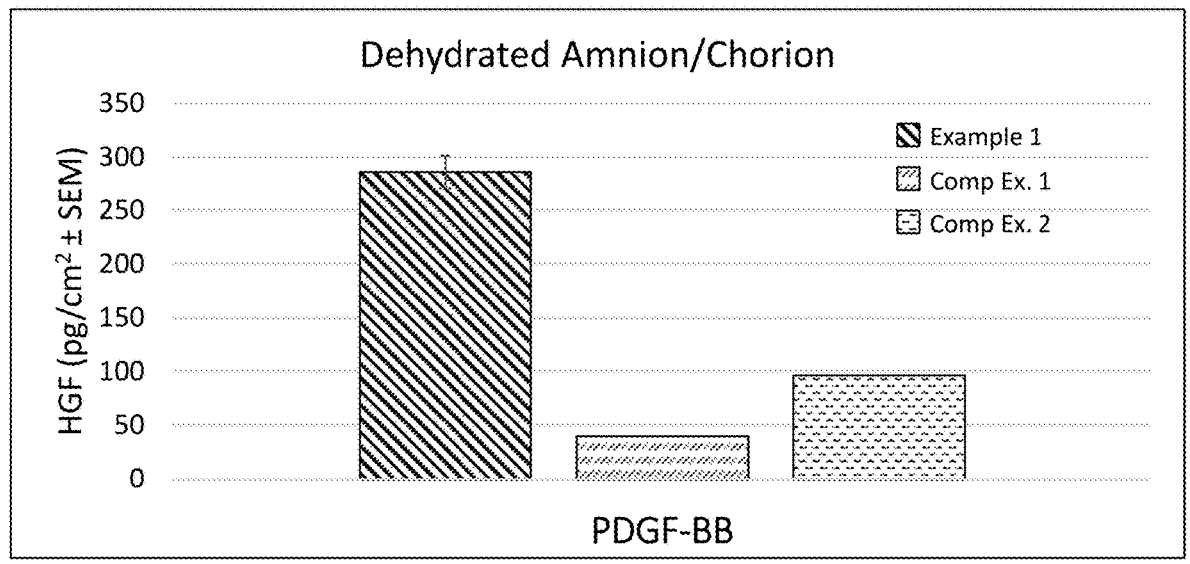
FIG. 8A depicts PDGF-BB concentrations in within Example 1.
Figure 8B:
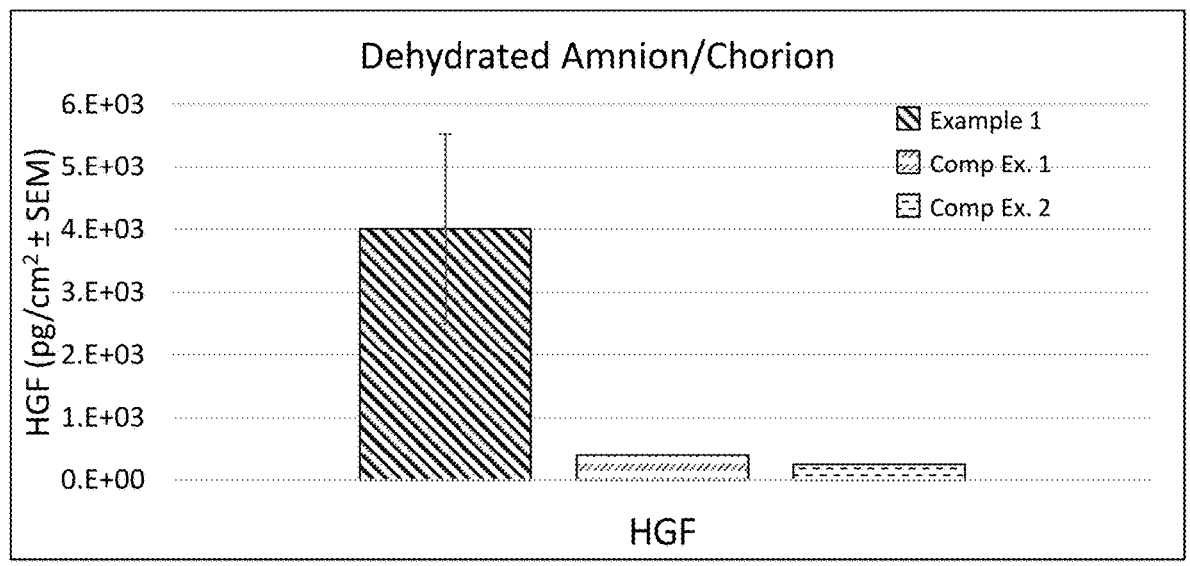
FIG. 8B depicts HGF concentrations within Example 1.
Figure 8C:
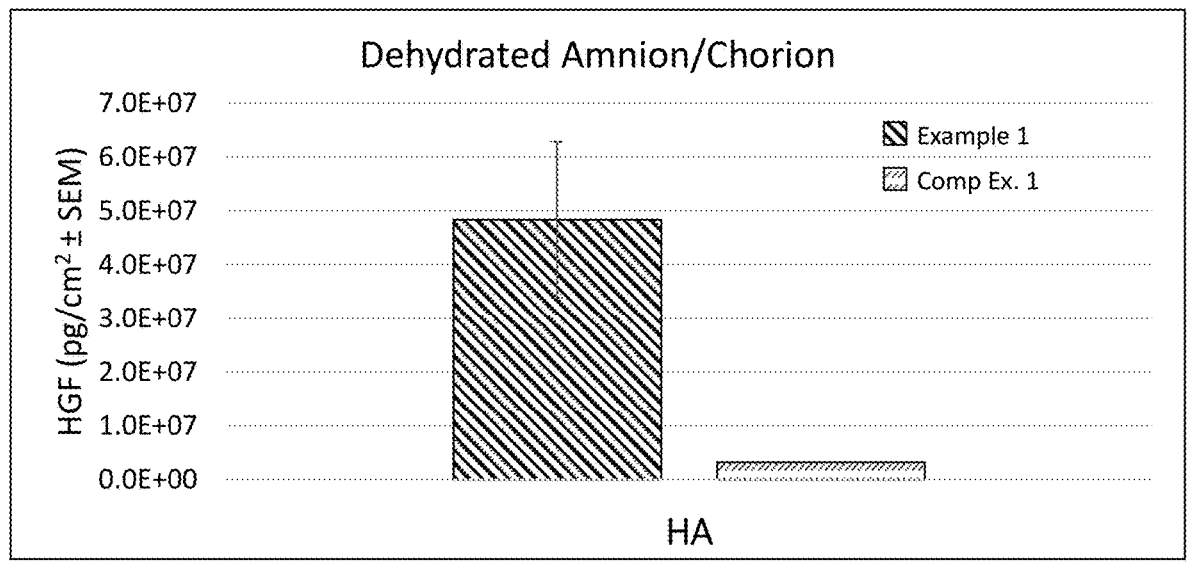
FIG. 8C depicts HA concentrations within Example 1.
Figure 10B:
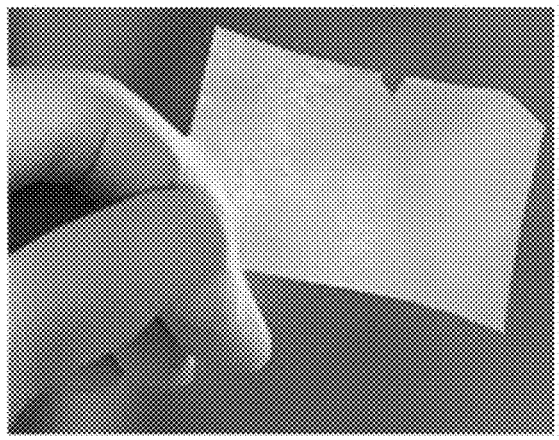
FIG. 10B is a photograph of the commercially available product of FIG. 8B (i.e., Comp Ex. 1)
Figure 10C:
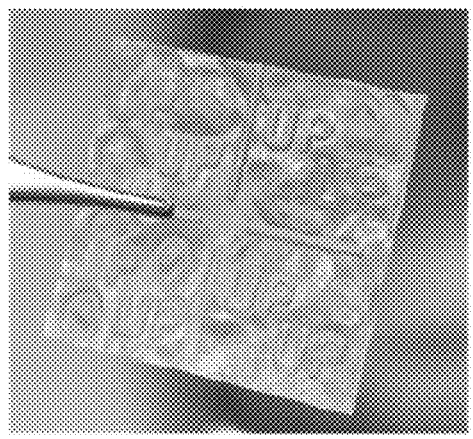
FIG. 10C is a photograph of the commercially available product of FIG. 8C (i.e., Comp Ex. 2)

FIG. 8A, FIG. 8B, and FIG. 8C are graphs depicting PDGF-BB, HGF, and HA concentrations within Example 1 (sterile human placental allograft disclosed herein with intact in cross-section in which the human amnion layer and the human chorion layer have an intact human intermediate spongy layer positioned there between connecting the human amnion layer to the human chorion layer) compared to commercially available sterile human placental allograft products having dehydrated amnion and chorion therein (i.e., Comparative Example 1 ("Comp Ex. 1") and Comparative Example 2 ("Comp. Ex. 2"). FIG. 10A is a photograph of the sterile human placental allograft of FIG. 8A (i.e., Example 1); FIG. 10B is a photograph of the commercially available product of FIG. 8B (i.e., Comp Ex. 1), and FIG. 10C is a photograph of the commercially available product of FIG. 8C (i.e., Comp Ex. 2).

It should be noted that Comparative Example 1 is a commercially available sterile human placental allograft composition (NUSHIELD® by Organogenesis that was prepared by the TUTOPLAST® process. The TUTOPLAST® process uses numerous harsh wash processes to remove all lipids, bacteria and soluble proteins, and is terminally sterilized by gamma radiation resulting in an end product that is a structural graft depleted of various growth factors.

It should be noted that Comparative Example 2 is a commercially available sterile human placental allograft composition (EPIFIX® by Mimedx prepared by the PURION® process and as further reported by Koob, et. al.

2013 and 2014), which separates the human amnion and human chorion layers, cleans them and then reattaches (laminates) the layers before dehydration.

As shown in FIGS. 8A, 8, and 8C, the sterile human placental allograft of Example 1 included considerably more of PDGF-BB, HGF, and HA (pg/cm$^2$) therein than either of Comparative Examples 1 and 2. The graphs provided in FIGS. 8A, 8B, and 8C are adjusted from mg to cm$^2$ by average weight of amnion/chorion per cm$^2$ (7.72 mg/cm$^2$). As further shown in FIGS. 8A, 8B, and 8C, Example 1 included an average of 320.31% more PDGF-BB than Comparative Examples 1 and 2, 1142.41% more HGF than Comparative Examples 1 and 2 and 1389.23% more HA than Comparative Example 1. These results clearly indicate retention and preservation of various endogenous growth factors in the human sterile placental allograft of Example 1 when compared with commercially available similar products. FIGS. 10A-10C further corroborate these results in which FIG. 10A (100), although translucent, is more opaque than the Comparative Examples 1 and 2 (FIGS. 10B and 10C respectively), which further indicates retention and preservation of various endogenous growth factors in the human sterile placental allograft of Example 1 when compared with commercially available similar products.

Figure 9:
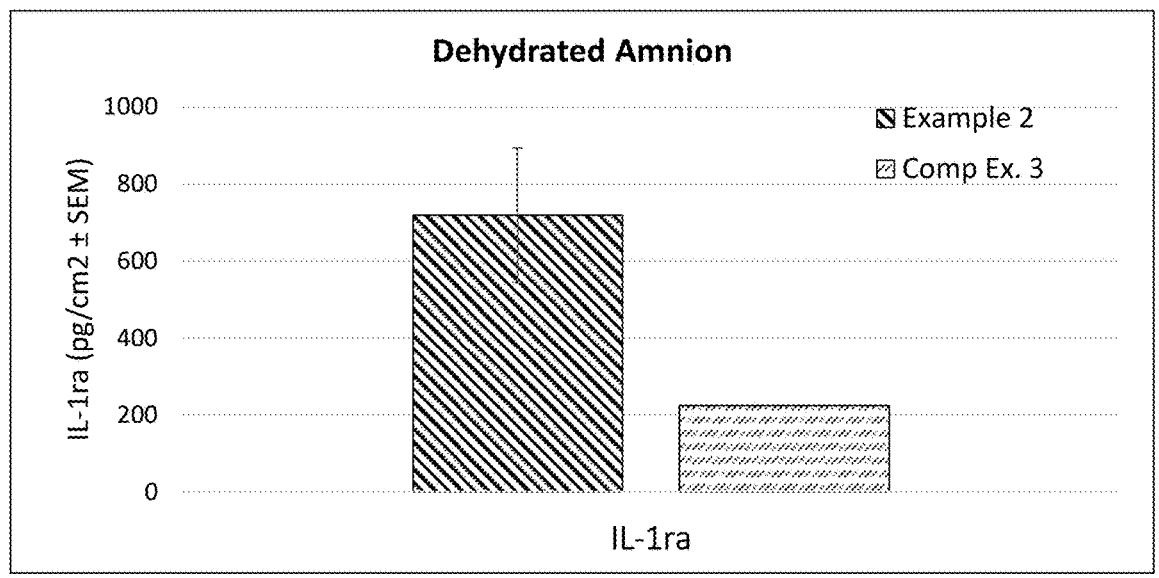
FIG. 9 is a graph depicting IL-1ra concentration within Example 2 (sterile human placental allograft disclosed herein that consists essentially of human amnion) compared to a commercially available product that only includes dehydrated amnion therein (i.e., Comparative Example 3 ("Comp Ex. 3")

FIG. 9 is a graph depicting IL-1ra concentration within Example 2 (sterile human placental allograft disclosed herein that consists essentially of human amnion) compared to a commercially available product that only includes dehydrated amnion therein (i.e., Comparative Example 3 ("Comp Ex. 3")). In particular, Comparative Example 3 is AMNIOFIX® amnion by Mimedx prepared by the PURION® process and as further reported by Koob, et. al. 2013 and 2014).

As shown in FIG. 9, the sterile human placental allograft of Example 1 included on average 220.88% more IL-1ra than Comparative Example 3, which clearly indicates retention and preservation of various endogenous growth factors in the human sterile placental allograft of Example 2 (i.e., sterile human placental allograft disclosed herein that consists essentially of human amnion prepared by the disclosed methods/processes herein) when compared with commercially available similar product of Comparative Example 3. Moreover FIGS. 11A and 11B further corroborate these results in which FIG. 11A (200), although translucent, is more opaque than the highly processed, translucent visual appearance of Comparative Example 3 (FIG. 11B), which further indicates retention and preservation of various endogenous growth factors in the human sterile placental allograft of Example 2 when compared with commercially available similar product.

The foregoing description provides embodiments of the invention by way of example only. It is envisioned that other embodiments may perform similar functions and/or achieve similar results. Any and all such equivalent embodiments and examples are within the scope of the present invention and are intended to be covered by the appended claims.

What is claimed is:

1. A sterile human placental allograft comprising a human amnion layer, an intact human intermediate spongy layer, and a human chorion layer, the sterile human placental allograft comprising interleukin-1 receptor antagonist (IL-1ra) ranging from 1000 to 6000 pg/cm$^2$ and hepatocyte growth factor (HGF) ranging from 600 to 7500 pg/cm$^2$; and at least one of the following:
   (a) vascular endothelial growth factor receptor 1 (VEGFR1);
   (b) hyaluronic acid (HA) ranging from $1.0 \times 10^7$ to $1.0 \times 10^8$ pg/cm$^2$;
   (c) platelet derived growth factor subunit B homodimer (PDGF-BB);
   (d) glycosaminoglycans (GAGs);
   (e) collagen; and
   (f) exosomes,
   wherein the sterile placental allograft is intact in cross-section in which the human amnion layer and the human chorion layer have an intact human intermediate spongy layer positioned between and connecting the human amnion layer to the human chorion layer, and
   the sterile placental allograft comprises a plurality of flaps formed through the sterile placental allograft, each flap of the plurality of flaps:
      opens by moving in a direction away from the lower surface of the sterile human placental allograft allowing for wound exudate to flow from a wound and passing through the sterile human placental allograft in a direction from a lower surface of the sterile human placental allograft to an upper surface of the sterile human placental allograft to facilitate wound drainage, wound healing, or a combination thereof, and
      closes by moving in a direction towards the lower surface of the sterile human placental allograft such that no opening remains when each flap of the plurality of flaps is closed.

2. The sterile human placental allograft of claim 1, wherein the sterile human placental allograft is configured for dental, cosmetic, and/or wound healing applications.

3. The sterile human placental allograft of claim 2, wherein the sterile human placental allograft comprises a predetermined size of from 1 cm×1 cm to 8 cm×8 cm for rectangular and/or square shaped sterile human placental allografts and from 8 mm diameter to 50 mm diameter for circular shaped sterile human placental allografts.

4. The sterile human placental allograft of claim 3, wherein the sterile human placental allograft comprises a circular shape, a square shape, a rectangular shape, an ovoid shape, a triangular shape, or any combination thereof.

5. The sterile human placental allograft of claim 1, wherein the upper and lower surfaces of the sterile human placental allograft are planar.

6. The sterile human placental allograft of claim 1, wherein the flap moves in a direction away from the lower surface and the upper surface of the sterile human placental allograft when open.

7. The sterile human placental allograft of claim 6, wherein the flap has a predetermined shape.

8. The sterile human placental allograft of claim 7, wherein the predetermined shape is a "V" shape, a "U" shape, a semi-"U" shape, or combinations thereof.

9. A kit comprising the sterile human placental allograft of claim 1.

10. A method of treating a wound in a human subject in need thereof comprising contacting the wound with a sterile human placental allograft of claim 1 for a predetermined time period to facilitate wound healing in the human subject in need thereof.

11. The method of claim 10, wherein the sterile human placental allograft is implanted in the subject in need thereof.

12. The method of claim 11, wherein the wound is an internal wound within the subject in need thereof and/or a dental wound.

13. The method of claim 10, wherein the sterile human placental allograft is topically applied to the wound in the human subject in need thereof.

14. The method of claim 10, wherein the wound is a diabetic ulcer.

\* \* \* \* \*